(12) United States Patent
Thompson et al.

(10) Patent No.: US 9,284,596 B2
(45) Date of Patent: Mar. 15, 2016

(54) METHODS FOR DETERMINING ENZYMATIC ACTIVITY COMPRISING HEATING AND AGITATION OF CLOSED VOLUMES

(71) Applicant: Battelle Energy Alliance, LLC, Idaho Falls, ID (US)

(72) Inventors: David Neil Thompson, Idaho Falls, ID (US); Emily DeCrescenzo Henriksen, Morrisville, NC (US); David William Reed, Idaho Falls, ID (US); Jill Renee Jensen, Buffalo Grove, IL (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 14/180,161

(22) Filed: Feb. 13, 2014

(65) Prior Publication Data

US 2015/0225765 A1 Aug. 13, 2015

(51) Int. Cl.
*C12Q 1/34* (2006.01)
*C12Q 1/40* (2006.01)

(52) U.S. Cl.
CPC ........................................ *C12Q 1/40* (2013.01)

(58) Field of Classification Search
CPC ........................................................ C12N 9/00
See application file for complete search history.

(56) References Cited

U.S. PATENT DOCUMENTS

| 4,788,150 | A | 11/1988 | Nelson et al. |
| 2013/0078625 | A1 | 3/2013 | Holmes et al. |
| 2013/0078662 | A1* | 3/2013 | Mano et al. ..................... 435/25 |

FOREIGN PATENT DOCUMENTS

| EP | 0195893 B1 | 6/1989 |
| WO | 2007022026 A2 | 2/2007 |
| WO | 2012058632 A1 | 5/2012 |
| WO | 2013052318 A1 | 4/2013 |

OTHER PUBLICATIONS

E-COEI-1-ACTPME-EN 2012, pp. 1-16.*
Fisher Scientific Isotemp Digital and Analog Dry Bath Incubators, www.fishersci.com/ecomm/servlet/productimagesview?catalogId=-1&productId=5001362&langId=-1&storeId=10652&distype=3&isChemical=false&selectedIma..., (accessed Oct. 15, 2013), 1 page.
Gusakov et al., "Comparison of Two Methods for Assaying Reducing Sugars in the Determination of Carbohydrase Activities," Int'l J. of Analytical Chemistry, vol. 2011, Article ID 283658, Hindawi Publishing Corporation, (2011), pp. 1-4.
"endo-1,4-β-XYLANASE M4 (from A. niger)," Megazyme, (Feb. 2013), 1 page.

* cited by examiner

*Primary Examiner* — Bin Shen
(74) *Attorney, Agent, or Firm* — TraskBritt

(57) ABSTRACT

Methods for determining thermophilic enzymatic activity include heating a substrate solution in a plurality of closed volumes to a predetermined reaction temperature. Without opening the closed volumes, at least one enzyme is added, substantially simultaneously, to the closed volumes. At the predetermined reaction temperature, the closed volumes are agitated and then the activity of the at least one enzyme is determined. The methods are conducive for characterizing enzymes of high-temperature reactions, with insoluble substrates, with substrates and enzymes that do not readily intermix, and with low volumes of substrate and enzyme. Systems for characterizing the enzymes are also disclosed.

20 Claims, 17 Drawing Sheets

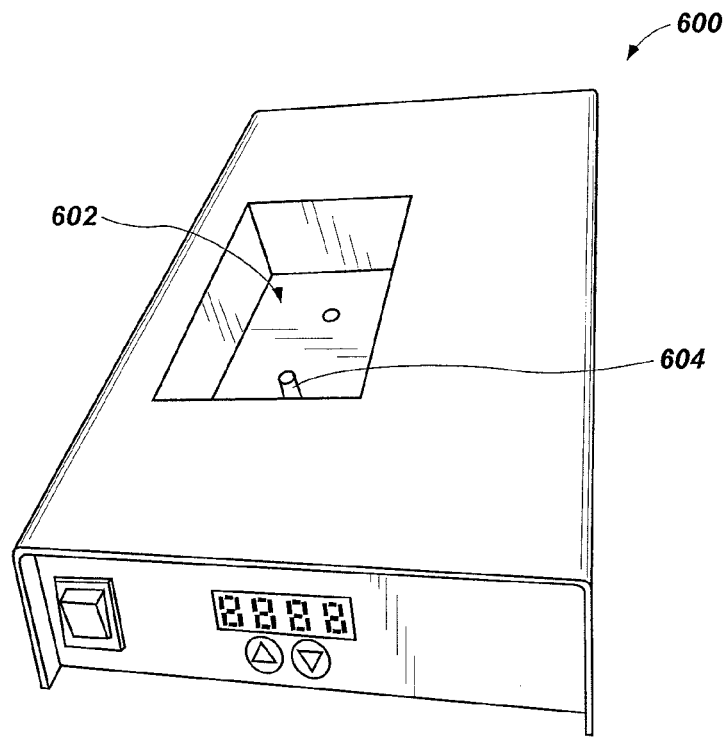
FIG. 6
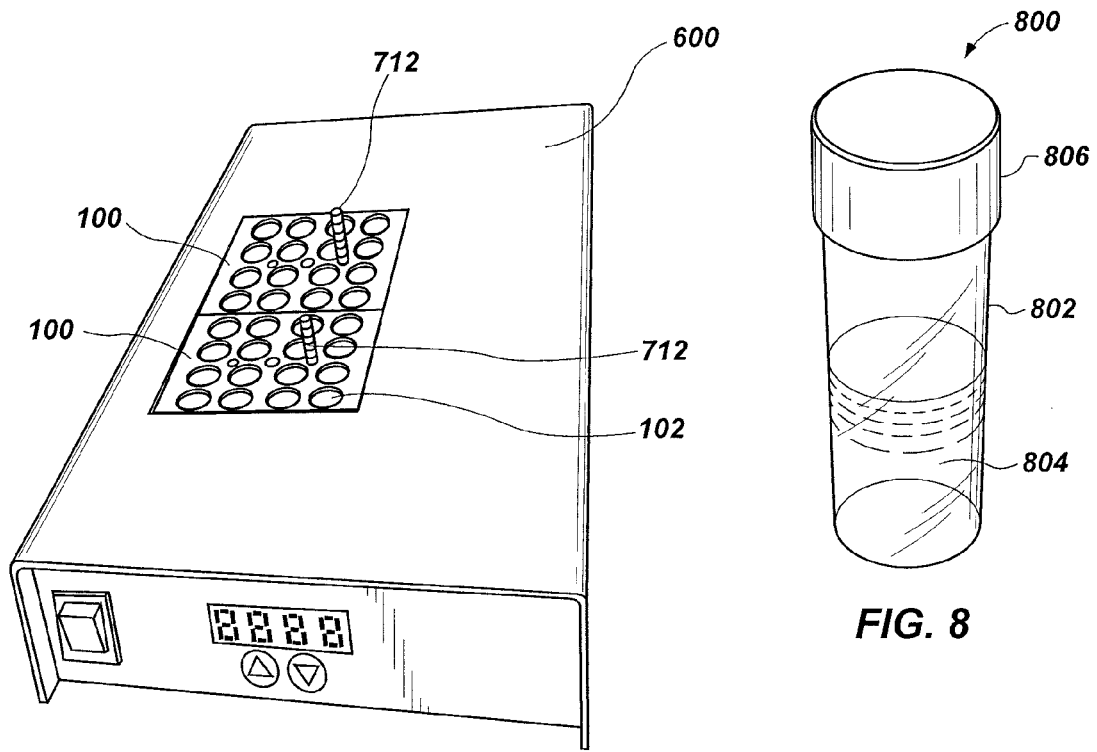
FIG. 7
FIG. 8

METHODS FOR DETERMINING ENZYMATIC ACTIVITY COMPRISING HEATING AND AGITATION OF CLOSED VOLUMES

STATEMENT REGARDING FEDERALLY SPONSORED RESEARCH OR DEVELOPMENT

This invention was made with government support under Contract No. DE-AC07-05-ID14517 awarded by the United States Department of Energy. The government has certain rights in the invention.

TECHNICAL FIELD

The present disclosure, in various embodiments, relates generally to the field of thermophilic enzyme characterization. More particularly, this disclosure relates to methods and systems for determining enzymatic activity. The methods and systems may be utilized for enzyme characterization studies applied to enzymatic reactions that involve, among others characteristics, high temperatures, insoluble substrates, and heterogeneous substrates.

BACKGROUND

Enzymes are biological molecules that catalyze a chemical reaction of a substrate. To understand the reaction mechanism and kinetics of such enzymatic reactions, it is often desirable to characterize an enzyme by determining its activity. Enzyme characterizations are carried out with assays that quantitatively assess enzyme activity based on, for example, resulting concentrations of one or more products of the enzymatic reaction. Thus, enzyme characterization provides information about the enzyme activity that can be used to predict how the enzyme will behave when reaction mixtures are altered, such as by adjusting the amounts of substrate, enzyme, etc., involved. Characterizing enzyme activity at different temperatures or pH levels provides information about the enzyme activity that can be used to predict how the enzyme will behave when reaction conditions are altered.

Typically, enzyme activity is determined by measuring the concentration of a reaction product of an enzymatic reaction over time for a fixed and constant enzyme concentration. Thus, the higher a reaction product concentration detected, in a period of time, the higher the enzyme activity determined. However, the reaction product concentration levels may be impacted by conditions other than enzyme activity. For example, some enzymatic reactions are carried out at high temperatures (e.g., at temperatures above about 50° C.) that can cause reagents of the reaction to evaporate, skewing concentration measurements. That is, if the reagents evaporate during the reaction, resulting concentrations of reaction products may be determined to be artificially higher than they would otherwise be, indicating a false-high enzymatic activity, or the evaporation may concentrate the enzyme in the reaction, resulting, again, in artificially high measured concentrations of reaction products. As another example, some substrates are generally insoluble in the reagents, and mass transfer properties, such as the diffusivity of the enzyme into the substrate or the diffusivity of a reaction product out of the substrate, may control the rate of the enzymatic reaction and, thus, the rate of production of the reaction product. Therefore, measured reaction product concentrations may be artificially low based on a low diffusivity value, rather than on the actual rate of the enzymatic reaction. As still another example, not all substrates and enzymes readily intermix with one another. Low intermixing may result in less enzymatic activity and, thus, low reaction product concentrations, even if the reaction rate is actually rapid.

Additionally, conventional methods for enzyme characterization may not be well suited to evaluate the enzymatic activity using substrates that are of industrial relevance. Not only may some industrially-relevant substrates be generally insoluble, but some may additionally or alternatively be generally heterogeneous such that one small sample of the substrate may vary in composition from another small sample of the same substrate. To try to avoid such heterogeneity impacting the results of enzymatic characterization methods, many conventional methods involve the use of a large amount of the substrate. However, use of a large amount of substrate may require use of a large amount of enzyme in the characterization. Such large-volume methods may not be conducive for characterizing enzymes for which only small amounts are available.

Thus, accurately characterizing enzymes for high-temperature (i.e., greater than about 50° C.) reactions, reactions with insoluble substrates, reactions with substrates and enzymes that do not readily intermix, reactions with heterogeneous substrates, or reactions where large quantities of enzymes or substrates are not available often presents challenges.

BRIEF SUMMARY

A method for determining enzymatic activity, according to an embodiment of the present disclosure, comprises heating a substrate solution in a plurality of closed volumes to a predetermined reaction temperature. Without opening the closed volumes of the plurality, at least one enzyme is substantially simultaneously added to the closed volumes of the plurality. After adding the at least one enzyme, the plurality of closed volumes are agitated at the predetermined reaction temperature. After the agitation, the activity of the at least one enzyme is determined.

A method for determining enzymatic activity, according to another embodiment of the present disclosure, comprises heating a conductive structure, supporting sealed reaction vessels containing substrate, to a predetermined reaction temperature. At least one enzyme is substantially simultaneously injected into the sealed reaction vessels. The sealed reaction vessels, with the substrate and the at least one enzyme, are agitated in a plane of motion parallel to a length of the sealed reaction vessels. The method also comprises determining activity of the at least one enzyme.

A system for determining enzymatic activity, according to an embodiment of the present disclosure, comprises a conductive structure that defines a plurality of wells protruding into the conductive structure from an upper surface of the conductive structure. The plurality of wells is configured to receive a plurality of reaction vessels. The conductive structure also defines at least one engagement feature on a sidewall of the conductive structure. The at least one engagement feature is configured to engage a counterpart engagement feature to secure the conductive structure to an agitator.

BRIEF DESCRIPTION OF THE DRAWINGS

FIG. 4 is also a rear elevation view of the conductive structure of FIGS. 1 through 3 with the lid on the conductive structure.

FIG. 5 is also a left side elevation view of the conductive structure of FIGS. 1 through 4 with the lid on the conductive structure.

FIGS. 6 through 17 are views of various stages of a method for processing an enzyme to be characterized, according to an embodiment of the present disclosure, wherein:

FIG. 6 is a top and front perspective view of a dry bath incubator into which the conductive structure of FIGS. 1 through 5 is configured to be received;

FIG. 7 is a top and front perspective view of the dry bath incubator of FIG. 6 having received therein two of the conductive structures of FIGS. 1 through 5 with alignment members received in the conductive structures;

FIG. 8 is a top and front perspective view of a fluid-containing vial that the conductive structure of FIGS. 1 through 5 is configured to receive;

FIG. 9 is an exploded view of a conductive structure assembly, including a top and rear perspective view of the conductive structure of FIGS. 1 through 5 with a plurality of the fluid-containing vials of FIG. 8 received in wells of the conductive structure and an alignment member received in the conductive structure, a bottom and rear perspective view of a lid to secure to the conductive structure, and a bottom and rear perspective view of a fastener member to secure the lid to the conductive structure;

FIG. 10 is a top, rear, and left side perspective view of the conductive structure assembly of FIG. 9, assembled for heating to a predetermined reaction temperature in the dry bath incubator of FIG. 6, with the lid secured to the conductive structure via the fastener member and another fastener engaged with the alignment member;

FIG. 11 is a partial, top, front, and left side perspective view of the conductive structure of FIGS. 1 through 5 in the dry bath incubator of FIG. 6 with a plurality of substrate-containing vials, some of which having lids with septa, and a top and front perspective view of a substrate-containing vial with a septum-containing lid to be received in a well of the conductive structure;

FIG. 12 is a top, front, and right side view of the two conductive structures of FIG. 7, in the dry bath incubator of FIG. 6, the conductive structures having received therein substrate-containing vials with septa-including lids, and with an injector support structure aligned over one of the two conductive structures;

FIG. 13 is a bottom, rear, and right side view of the injector support structure of FIG. 12;

FIG. 14 is a front, cross-sectional, elevation view, taken along section line 14-14 of FIGS. 11 and 12, with injectors received in conduits of the injector support structure of FIG. 12, needles of the injectors extending through septa of substrate-containing vials, and the lid of FIG. 9 being utilized to simultaneously depress plungers of the injectors to substantially simultaneously inject at least one enzyme from the injectors into a liquid in the substrate-containing vials;

FIG. 15 is a top, front, and right side perspective view of a support structure secured to a shaker plate of an orbital shaker;

FIG. 16 is a front, cross-sectional, elevation view, of the conductive structure of FIGS. 4 and 5, taken along section line 16-16 of FIG. 15, having an engagement feature engaged with a counterpart engagement feature of the support structure of FIG. 15; and FIG. 17 is a top, front, and left side perspective view of a conductive structure assembly such as that of FIG. 10, but having received therein substrate-and-enzyme containing vials, secured to the shaker plate of an orbital shaker via the support structure of FIG. 15 and being agitated in a plane of motion that is parallel to a length of the substrate-and-enzyme containing vials while a predetermined reaction temperature is maintained.

DETAILED DESCRIPTION

Methods and systems for determining activity of an enzyme are disclosed. Substrate in closed vessels is brought to a predetermined reaction temperature. Without opening the vessels, at least one enzyme is substantially simultaneously added to each of the closed vessels. The closed vessels, with the substrate and added enzyme, are then agitated to mix the substrate and the enzyme. The closed vessels may be maintained at essentially the predetermined reaction temperature throughout the enzyme addition and the agitation. Therefore, the temperature may be controlled, evaporation of reagents may be prevented, and multiple samples may be simultaneously processed, increasing the throughput. The enzymatic reactions, which take place in the closed vessels, may be analyzed to accurately determine enzyme activity, even for high-temperature enzymatic reactions, insoluble substrates, substrates and enzymes that do not readily intermix, substrates that are heterogeneous, and low sample sizes of the substrate and enzyme. Thus, the activity of enzymes for enzymatic reactions that involve insoluble substrates, partially-soluble substrates, heterogeneous substrates, small substrate amounts, small enzyme volumes, high-temperatures, or mixing challenges may be determined by a reliable and reproducible method. The methods and systems of the present disclosure may also provide a high throughput assay for determining the enzymatic activity.

The illustrations presented herein are not meant to be actual views of any particular apparatus, system, or method stage, but are merely idealized representations that are employed to describe embodiments of the present invention.

As used herein, the term "substrate" means and includes a material to be at least partially consumed in a reaction catalyzed by the at least one enzyme to be characterized.

The following description provides specific details, such as material types and processing conditions in order to provide a thorough description of embodiments of the present disclosure. However, a person of ordinary skill in the art will understand that the embodiments of the present disclosure may be practiced without employing these specific details. The embodiments of the present disclosure may be practiced in conjunction with conventional enzyme characterization methods known in the industry, utilizing the results of the methods of processing the enzymes disclosed herein and/or the systems for processing the enzymes disclosed herein.

Unless the context indicates otherwise, the structures described herein may be formed by any suitable technique, the samples may be prepared by any suitable technique, and the enzymatic reactions may be analyzed by any suitable technique, which techniques may be selected by a person having ordinary skill in the art.

Figure 4:
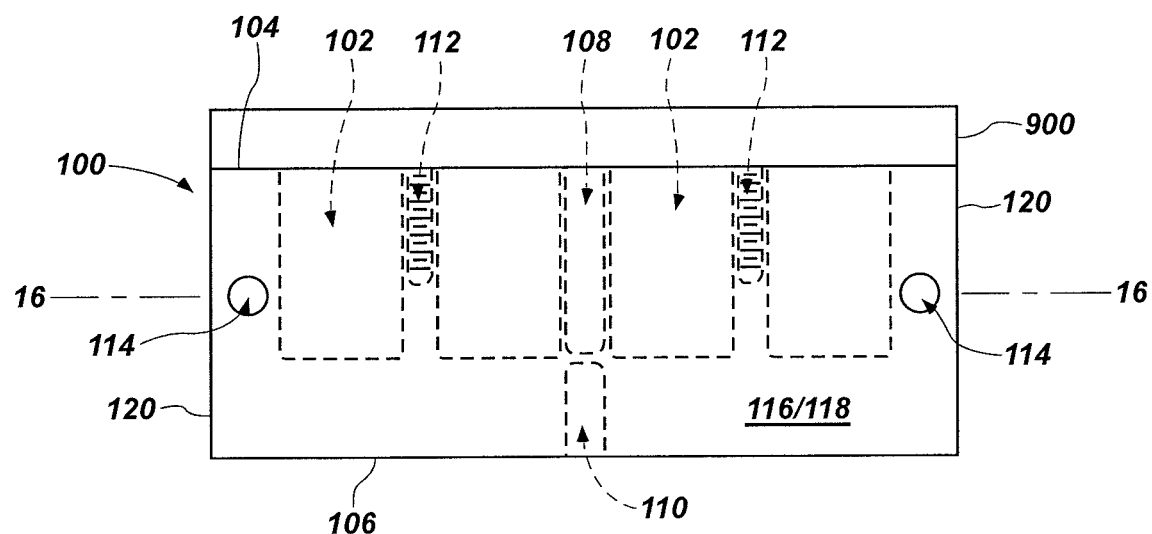
FIG. 4 is a front elevation view of the conductive structure of FIGS. 1 through 3 with a lid on the conductive structure.

FIGS. 1 through 5 illustrate a conductive structure 100 configured to receive and transfer heat to reaction vessels. Substrate samples and at least one enzyme may be inserted into the reaction vessels, and enzymatic reactions may be carried out before the results of the reaction are analyze to characterize the enzyme. The conductive structure 100 may include a number of wells 102 that protrude into the conductive structure 100 from an upper surface 104 of the conductive structure 100. As illustrated in FIG. 4, the wells 102 may protrude essentially perpendicularly relative to the upper surface 104 and to a lower surface 106. The wells 102 may be shaped to snugly receive therein the reaction vessels. Therefore, heat may be conductively transferred between the conductive structure 100 and the reaction vessels.

The conductive structure 100 may be formed of a conductive material, such as, for example and without limitation, a metal (e.g., aluminum), a metal alloy, or other conductive material. The conductive material may be selected to have a high heat conductivity, so that the conductive structure 100 may be quickly heated by a heat source, and a high heat capacity, so that the conductive structure 100 remains heated even if the heat source is temporarily interrupted.

The conductive structure 100 may be formed from an essentially-solid block of the conductive material. The wells 102, and other negative-space features, may be machined or otherwise formed into the block by conventional techniques, which are not described in detail herein. In other embodiments, the conductive structure 100 may be molded to define the wells 102, and other negative-space features, when the conductive material is first formed into the conductive structure 100.

Figures 1, 2:
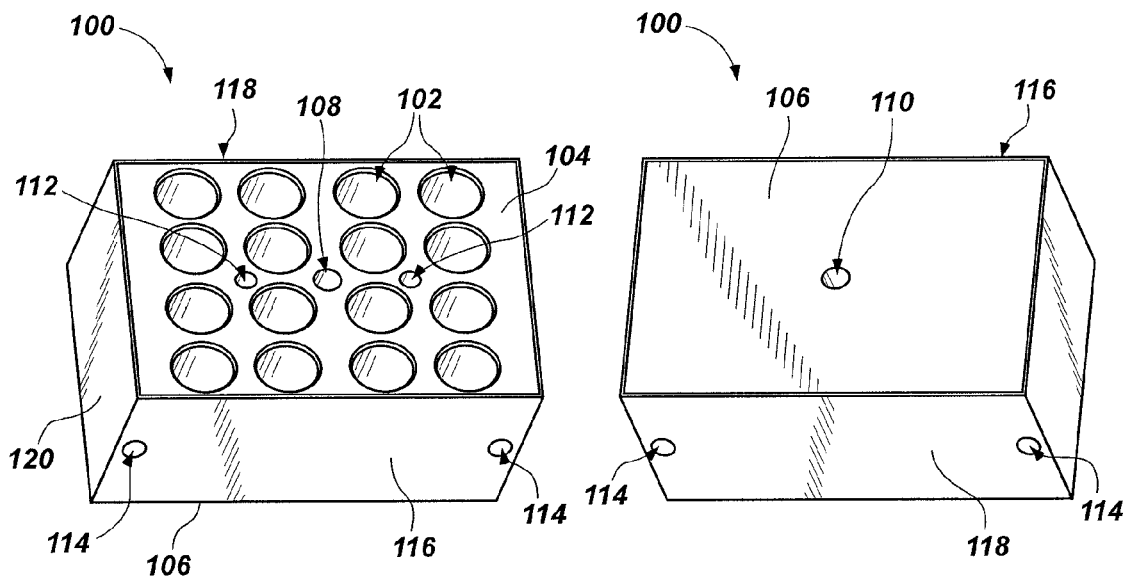
FIG. 1 is a top, front, and right side perspective view of a conductive structure of a system for analyzing an enzyme, according to an embodiment of the present disclosure.
FIG. 2 is a bottom, rear, and left side perspective view of the conductive structure of FIG. 1.
Figure 3:
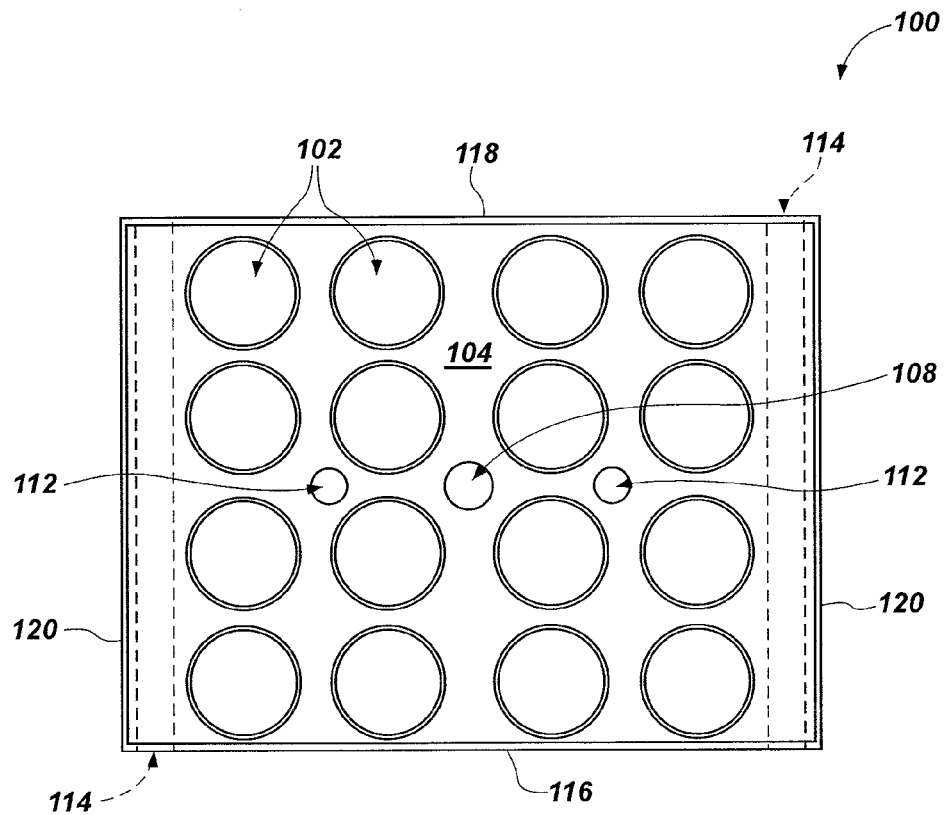
FIG. 3 is a top, plan view of the conductive structure of FIGS. 1 and 2.

The wells 102 may be arranged in an ordered array, e.g., the column-and-row arrangement illustrated in FIG. 1, or may be arranged without a particular order. In some embodiments, each of the wells 102 may have essentially the same dimensions and be evenly spaced. In other embodiments, the wells 102 may vary in dimension from one to another and not be evenly spaced. The dimensions and arrangement of the wells 102 may be tailored to enable heat transfer from the conductive structure 100 with consistent temperatures in the wells 102 regardless of the relative position of each well 102 in the conductive structure 100.

The conductive structure 100 may also define therein one or more probe openings. For example, a thermometer opening 108 may protrude into the conductive structure 100 from the upper surface 104. The thermometer opening 108 may be configured to receive therein a thermometer during heating and/or reaction stages of methods according to embodiments of the present disclosure. The thermometer opening 108 may protrude to, e.g., a depth approximately even with a depth of the wells 102, as illustrated in FIG. 4. Thus, temperatures read from a thermometer received in the thermometer opening 108 may be the same temperatures of materials within the reaction vessels received in the wells 102. To enable efficient heat transfer between walls of the thermometer opening 108 and the thermometer, the thermometer opening 108 may be filled with a heat transfer liquid (e.g., water or other fluid, e.g., oil) before the thermometer is received. The same heat transfer liquid may also be filled, partially or completely, into the wells 102 before the reaction vessels are received therein to, again, enable efficient heat transfer between the conductive material of the conductive structure 100 and the material of the reaction vessels.

In some embodiments, the conductive structure 100 may also define therein a thermocouple opening 110 configured to receive a thermocouple extending from a heating device. The thermocouple opening 110, as illustrated in FIGS. 2 and 4, may protrude into the conductive structure 100 from the lower surface 106. With reference to FIG. 4, the thermocouple opening 110 may align with the thermometer opening 108, though the two openings may not connect.

The conductive structure 100 may also define therein one or more openings 112 for receiving an alignment member and/or fastener member. For example, the openings 112 may be defined to protrude into the conductive structure 100 from the upper surface 104. In some embodiments, the openings 112 may be threaded and therefore configured to receive threaded alignment or threaded fastener members therein. With reference to FIG. 4, in some embodiments, the openings 112 may protrude to a depth less than that of the wells 102. However, in other embodiments, the openings 112 may protrude deeper or all the way through the height of the conductive structure 100.

In some embodiments, the conductive structure 100 may include an engagement feature configured to engage with a counterpart engagement feature of another structure to secure the conductive structure 100 to the other structure. For example, the engagement feature may include one or more openings 114 defined in a front surface 116 and a back surface 118 of the conductive structure 100 and extending through a length of the conductive structure 100. Therefore, counterpart engagement features (e.g., engagement features 1510 (FIG. 15)) may be received through the openings 114 and may be utilized to secure the conductive structure 100 to another structure such as, for example, an agitator.

Figure 5:
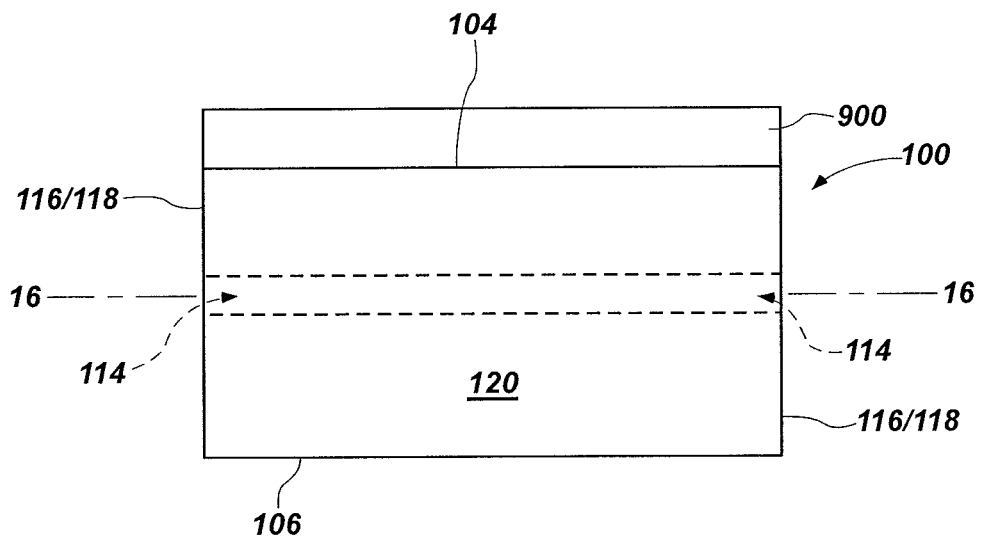
FIG. 5 is a right side elevation view of the conductive structure of FIGS. 1 through 4 with the lid on the conductive structure.

In some embodiments, side surfaces 120 of the conductive structure 100 may be free from openings, as illustrated in FIGS. 1 and 5.

Though the conductive structure 100 of FIGS. 1 through 5 is illustrated to be a six-sided block shape, in other embodiments, the conductive structure 100 may be otherwise shaped but nonetheless configured to receive reaction vessels in wells 102.

A method, according to an embodiment of the present disclosure, for characterizing an enzyme may include heating the conductive structure 100. Heat may be provided to the conductive structure 100 from a heat source such as a dry bath incubator 600, illustrated in FIG. 6. The dry bath incubator 600 may include a cavity 602 into which the conductive structure 100 (FIGS. 1 through 5) is received. A thermocouple 604 may protrude from a base of the cavity 602 and may be received in the thermocouple opening 110 (FIG. 4) of the conductive structure 100 (FIGS. 1 through 5) when the conductive structure 100 is in place in the cavity 602.

In some embodiments, the conductive structures 100 (FIGS. 1 through 5) are configured such that more than one conductive structure 100 may be received in the cavity 602 of the dry bath incubator 600, as illustrated in FIG. 7. The upper surface 104 (FIG. 1) of the conductive structure 100 may be flush with an upper surface of the dry bath incubator 600.

FIG. 7 further illustrates alignment members 712 received within one of the openings 112 (FIG. 4) defined in the conductive structures 100. The alignment members 712 may be threaded rods that are screwed into one of the openings 112 of the conductive structure 100 in such embodiments in which the openings 112 are also threaded. Therefore, in some embodiments, the alignment members 712 may be removable from the conductive structures 100. In other embodiments, the alignment members 712 may be permanently affixed to the conductive structures 100.

In some embodiments, the conductive structures 100 may be heated, using the dry bath incubator 600, to, e.g., a predetermined reaction temperature. The reaction temperature may be selected based on the enzymatic reaction to be carried out. In some such embodiments, the conductive structures 100 may be heated when empty, i.e., without any material received in the wells 102. In other embodiments, the wells 102 may be filled with a heat transfer fluid (e.g., water, oil, or other fluid) prior to or during the heating. The heat transfer fluid may also be added to the thermometer opening 108 (FIG. 4) as discussed above. In one embodiment, according to the present disclosure, the heat transfer fluid may be added to vessels 800 (FIG. 8) before or while they are received in the wells 102. The vessels 800 (FIG. 8) may be essentially the same as those to be used as reaction vessels later in the method. For example, a glass vial 802 may be used as the vessel 800, and water 804 may be added to the glass vial 802 and used as the heat transfer fluid. The volume of water 804 added may be approximately the same volume as the reagents of the enzymatic reaction to be carried out later in the method. Therefore, during the initial heating of the conductive structures 100 (FIG. 7), the heat to be provided to the later-received reaction vessels will be consistent with the heat provided to the vessels 800 with only the water 804. The vessels 800 may be sealed with a lid 806 that secures to the glass vial 802.

Figure 9:
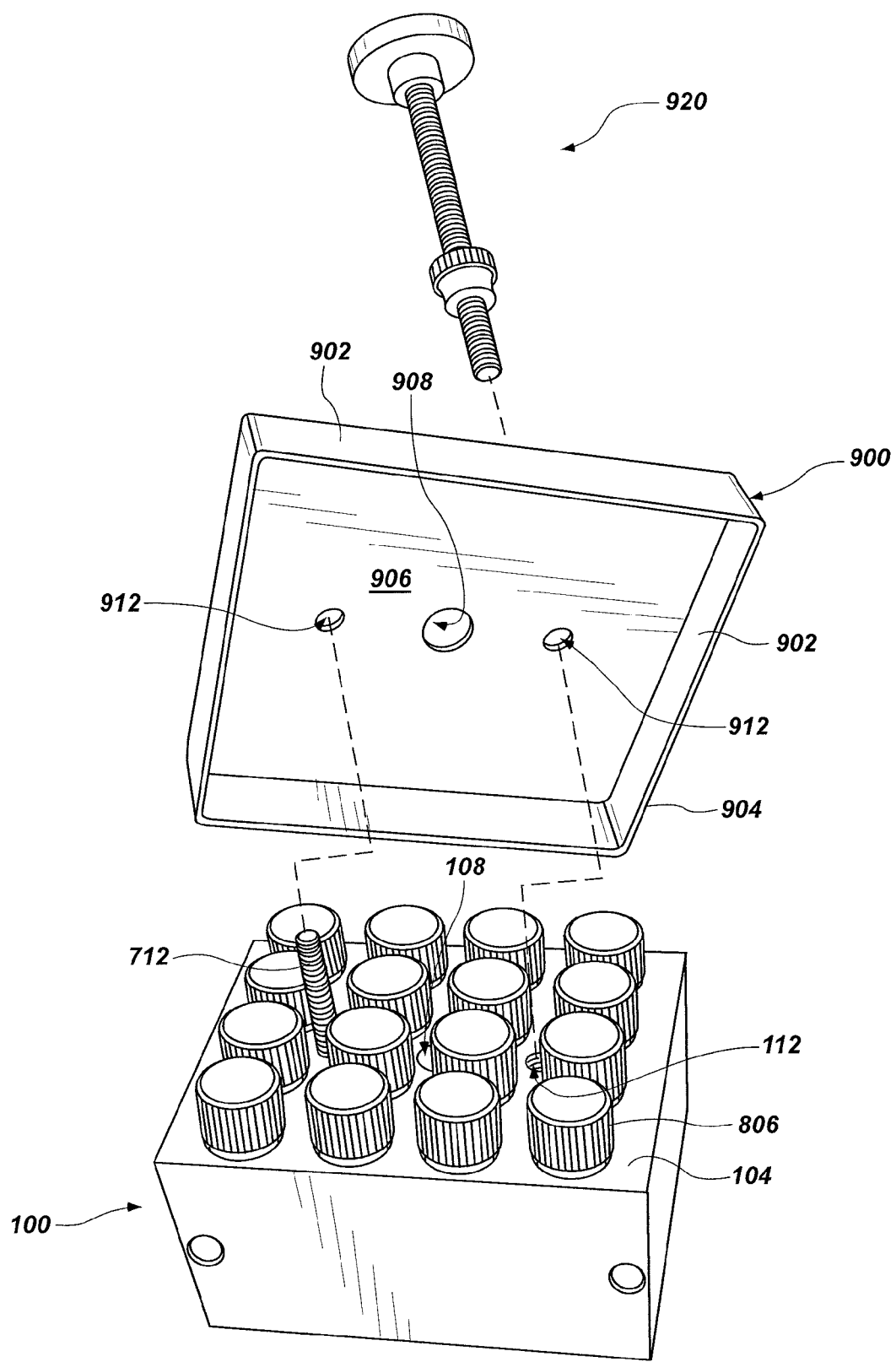

A vessel 800 may be loaded into each of the wells 102 (FIG. 7) so that the heat profile across the conductive structure 100 will be even. Each well 102 may be configured to snugly receive one of the vessels 800. In some embodiments, the walls of the glass vials 802 may be fully received in the wells 102 with essentially only the lids 806 protruding above the upper surface 104 of the conductive structure 100, as illustrated in FIG. 9. Thus, an even heat may be provided from the conductive structure 100 to the glass vials 802 (FIG. 8) and thereafter to the water 804 (FIG. 8) within the glass vials 802. In some embodiments, heat transfer fluid (e.g., additional water, oil) may be included in the wells 102 (FIG. 4) before the glass vials 802 are received therein to further ensure conductive heat transfer between the conductive structure 100 and the water 804 within the glass vials 802.

As illustrated in FIG. 9, a lid 900 may be placed over the top of the conductive structure 100 and over the lids 806 of the vessels 800 (FIG. 8). The lid 900 may have sidewalls 902 that extend the height of the lids 806 of the vessels 800 such that a lower edge 904 abuts the upper surface 104 of the conductive structure 100, as illustrated in FIGS. 4 and 5. An interior surface 906 of the lid 900 may abut the tops of the lids 806 of the vessels 800 (FIG. 8), when the lid 900 is secured to the conductive structure 100. When placed on the conductive structure 100, the lid 900 may reduce or prevent heat from exiting the conductive structure 100 and the vessels 800 (FIG. 8). Thus, the lid 900 may promote efficient heating of the vessels 800.

In some embodiments, the lid 900 may be formed of a conductive material (e.g., a metal (e.g., aluminum, tin), a metal alloy). The sidewalls 902 of the lid 900 may define a space in which each of the lids 806 of the vessels 800 (FIG. 8) may be received, as illustrated in FIG. 9. In another embodiment (not shown), the lid 900 may be formed as an essentially solid structure of a conductive material with wells configured to receive, in each, the lid 806 of one of the vessels 800. Thus, the lids 806 of the vessels 800 may be snugly received within the lid 900 on the conductive structure 100.

The lid 900 may define therein openings 912 that may align with the openings 112 defined in the upper surface 104 of the conductive structure 100. Therefore, the alignment member 712, received within one of the openings 112 of the conductive structure 100 may align with and extend through one of the openings 912 in the lid 900. A fastener, such as a nut 1012 (see FIG. 10) may be releaseably engaged with the alignment member 712 to secure the lid 900 to the conductive structure 100. A fastener member 920 may be passed through another of the openings 912 in the lid 900 to engage another of the openings 112 of the conductive structure 100. The fastener member 920 may be a threaded rod that corresponds to threading in the openings 112. The fastener member 920 may be screwed into the opening 112 to secure the lid 900 to the conductive structure 100. Thus, as illustrated in FIG. 10, a conductive structure assembly 1000 may be secured as the dry bath incubator 600 (FIG. 6) heats the conductive structure 100.

The lid 900 may define a thermometer opening 908 passing through the lid 900 and corresponding to the thermometer opening 108 of the conductive structure 100. Therefore, when the lid 900 is secured to the conductive structure 100, a thermometer may be inserted into the thermometer openings 108, 908 to monitor a temperature of the conductive structure 100.

Figure 10:
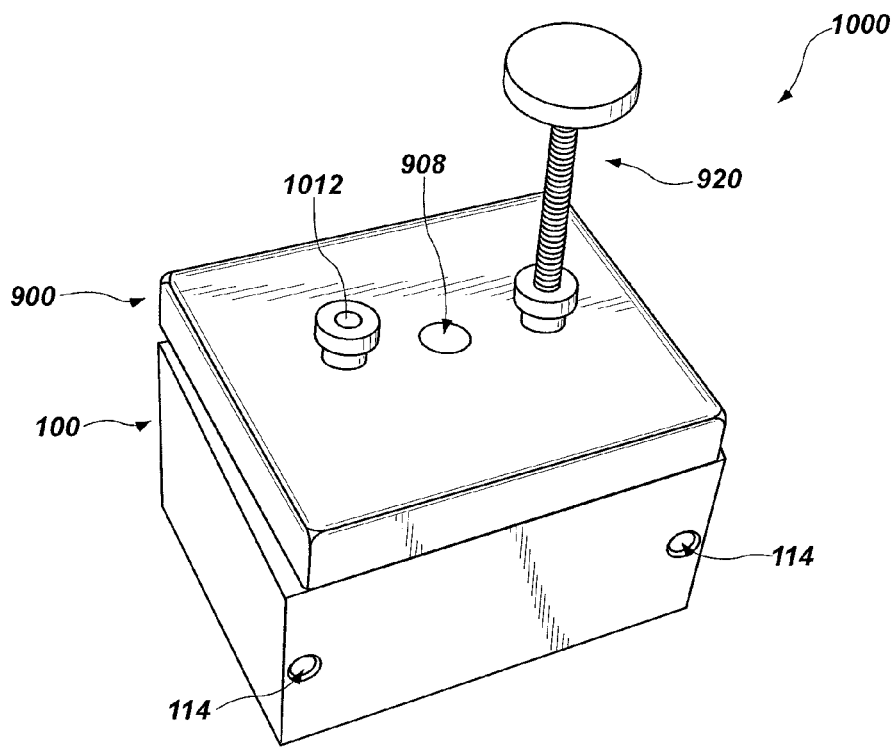

Though FIGS. 9 and 10 illustrate the conductive structure 100 out of the dry bath incubator 600 (FIG. 6) for convenience, it is contemplated that the conductive structure assembly 1000 will be assembled while the conductive structure 100 is received within the cavity 602 (FIG. 6) of the dry bath incubator 600 (FIG. 6) to allow the heating to continue without interruption while the lid 900 is secured to the conductive structure 100.

Figure 11:
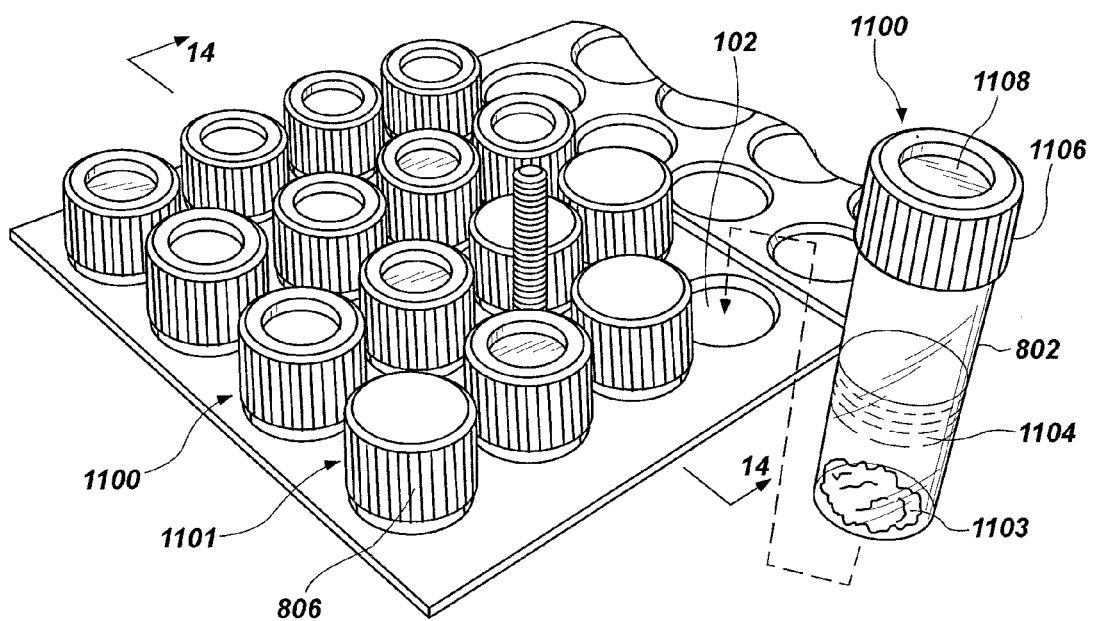

Once the conductive structure 100 is heated to the predetermined reaction temperature, as indicated by one or both of a thermometer in the thermometer opening 108 (FIG. 1) and a thermocouple in the thermocouple opening 110 (FIG. 4), the vessels 800 (FIG. 8) with the heat transfer fluid (e.g., water, oil) may be removed from the conductive structure 100 and quickly replaced with other vessels, such as, as illustrated in FIG. 11, reaction vessels 1100 or control vessels 1101. Each of the reaction vessels 1100 may include one of the glass vials 802 with a substrate sample 1103 therein and, for example, a buffer fluid 1104. The composition and amount of the substrate sample 1103 and the buffer fluid 1104 may be selected according to the enzymatic reaction to be carried out in the reaction vessel 1100. The substrate samples 1103 may be sealed in the reaction vessels 1100 by lids 1106 having septa 1108 that are penetrable by injection needles without unsealing the contents of the reaction vessels 1100. The control vessels 1101 may each include a control composition against which an enzymatic reaction to be carried out in one of the reaction vessels 1100 is to be compared. For control compositions into which no enzyme is to be added, the control vessels 1101 may be sealed by one of the lids 806 that does not include the septum 1108.

As illustrated in FIG. 11, each of the wells 102 may receive either one of the reaction vessels 1100 or one of the control vessels 1101. Reaction vessels 1100 may occupy all of the wells 102 of the conductive structure 100 (FIG. 10), control vessels 1101 may occupy all of the wells 120, or a mixed grouping of the reaction vessels 1100 and the control vessels 1101 may be used to occupy the wells 102. The grouping and disposition of the reaction vessels 1100 and/or control vessels 1101 used may be selected to provide the desired number of reaction results and controls against which to compare the reaction results.

In some embodiments, the same substrate sample 1103 may be included in each reaction vessel 1100. In other embodiments, a variety of substrate samples 1103 may be included in the reaction vessels 1100 and enzymatic reactions carried out in each simultaneously. In such embodiments, it is contemplated that the substrate samples 1103 will be selected so that reaction conditions, such as temperature, may be consistent for each of the reactions.

The vessels 800 (FIG. 8) used during the initial heating of the conductive structure 100 to the predetermined reaction temperature may be quickly replaced with the reaction vessels 1100 and/or the control vessels 1101 while the lid 900 (FIG. 10) is removed from the conductive structure 100. With minimal time used to switch out the vessels, minimal heat may be lost from the conductive structure 100. In some embodiments, e.g., such as those embodiments in which the disclosed methods are automated, all of the vessels 800 (FIG. 8) may be simultaneously removed and may be simultaneously replaced with the reaction vessels 1100 and/or the control vessels 1101, which may minimize the transition time and the heat lost.

It is contemplated that the volume of the water 804 (FIG. 8) in the vessels 800 (FIG. 8), used for the initial heating of the conductive structure 100 to the predetermined reaction temperature and later replaced with the controlled volumes (e.g., the reaction vessels 1100 and/or control vessels 1101), will be substantially the same as the volume of the buffer fluid 1104, and any other solid or liquid material, in the vessels (e.g., the reaction vessels 1100 and/or control vessels 1101). Therefore, the heat profile of the vessels 800 (FIG. 8), used for the initial pre-heating, will be substantially similar to the heat profile of the vessels (e.g., the reaction vessels 1100 and/or control vessels 1101), prior to enzyme injection. In other embodiments, the volumes may vary.

After replacing the initial vessels 800 (FIG. 8) with the other vessels (e.g., the reaction vessels 1100 and/or the control vessels 1101), the lid 900 (FIG. 10) may be again secured to the conductive structure 100 (FIG. 10) and the temperature of the conductive structure 100 monitored until the conductive structure assembly 1000 (FIG. 10) returns to the predetermined reaction temperature. Because the conductive structure 100 (FIG. 10) may be pre-heated to the predetermined reaction temperature before the control volumes (e.g., the reaction vessels 1100 and/or the control vessels 1101) are received in the wells 102 (FIG. 1) of the conductive structure 100 (FIG. 10), the time needed for the conductive structure 100 to return to the predetermined reaction temperature after the vessels (e.g., the reaction vessels 1100 and/or the control vessels 1101) are inserted may be minimal.

Though in some embodiments, the conductive structure 100 may be first heated to the predetermined reaction temperature with the substrate-free vessels 800 (FIG. 8) before the substrate samples 1103 are added to the system, in other embodiments, the conductive structure 100 may be first heated to the predetermined reaction temperature with the other vessels (e.g., the reaction vessels 1100 and/or the control vessels 1101) in the wells 102 (FIG. 1), including the substrate samples 1103. Whether or not the substrate samples 1103 are included in the initial heating of the conductive structure 100 may depend on whether the material of the substrate samples 1103 will decompose during the heating.

Once the system with the substrate samples 1103 is brought to the predetermined reaction temperature, the lid 900 (FIG. 10) may again be removed and at least one enzyme substantially simultaneously added to each of the reaction vessels 1100 to begin an enzymatic reaction in each of the reaction vessels 1100. The enzyme may be added into the reaction vessels 1100 through the septa 1108 such that the reaction vessels 1100 remain sealed. Keeping the reaction vessels 1100 sealed may reduce or prevent evaporation of reagents from the closed volumes of the reaction vessels 1100 and, therefore, prevent skewing of resulting concentration measurements.

Figure 12:
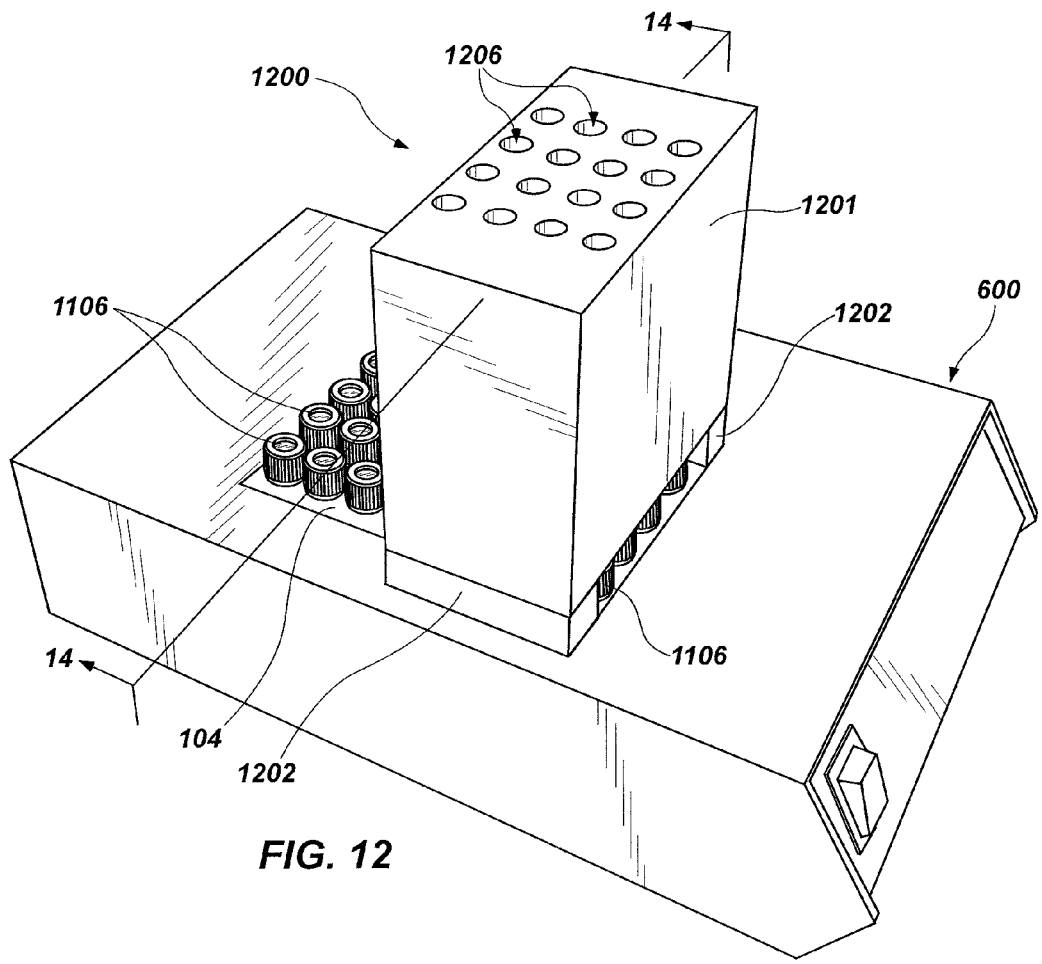
Figure 13:
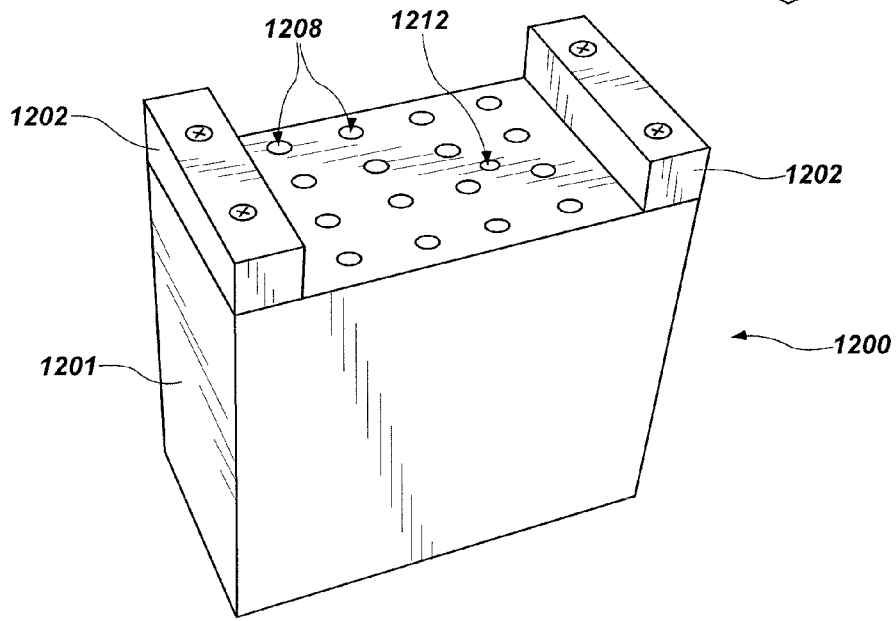

With reference to FIGS. 12 and 13, an injector support structure 1200 may be utilized to enable simultaneous addition of at least one enzyme to the reaction vessels 1100 (FIG. 11). The injector support structure 1200 may include a supportive body 1201 and extensions 1202 protruding from a bottom of the supportive body 1201. The injector support structure 1200 may be made of a solid material that is conductive (e.g., metal, metal alloy) or nonconductive (e.g., wood, plastic). The extensions 1202 may protrude a height at least as great as the height of the lids 1106 of the reaction vessels 1100 (FIG. 11) and control vessels 1101 (FIG. 11). The extensions 1202 may be spaced from one another by a width that is at least as great as a width of the reaction vessels 1100 and control vessels 1101 in the conductive structure 100 (FIG. 1). Therefore, the injector support structure 1200 may be positioned over the conductive structure 100 (FIG. 1) and the reaction vessels 1100 and control vessels 1101 retained therein, as illustrated in FIG. 12. In some embodiments, the extensions 1202 are configured to sit on an upper surface of the dry bath incubator 600, flush with the upper surface 104 of the conductive structure 100 (FIG. 1).

The injector support structure 1200 may be formed as a unitary body comprising the supportive body 1201 and the extensions 1202. Alternatively, the supportive body 1201 and the extensions 1202 may be separately formed and then assembled together by, for example and without limitations, fasteners (e.g., nails, screws, adhesive).

Figure 14:
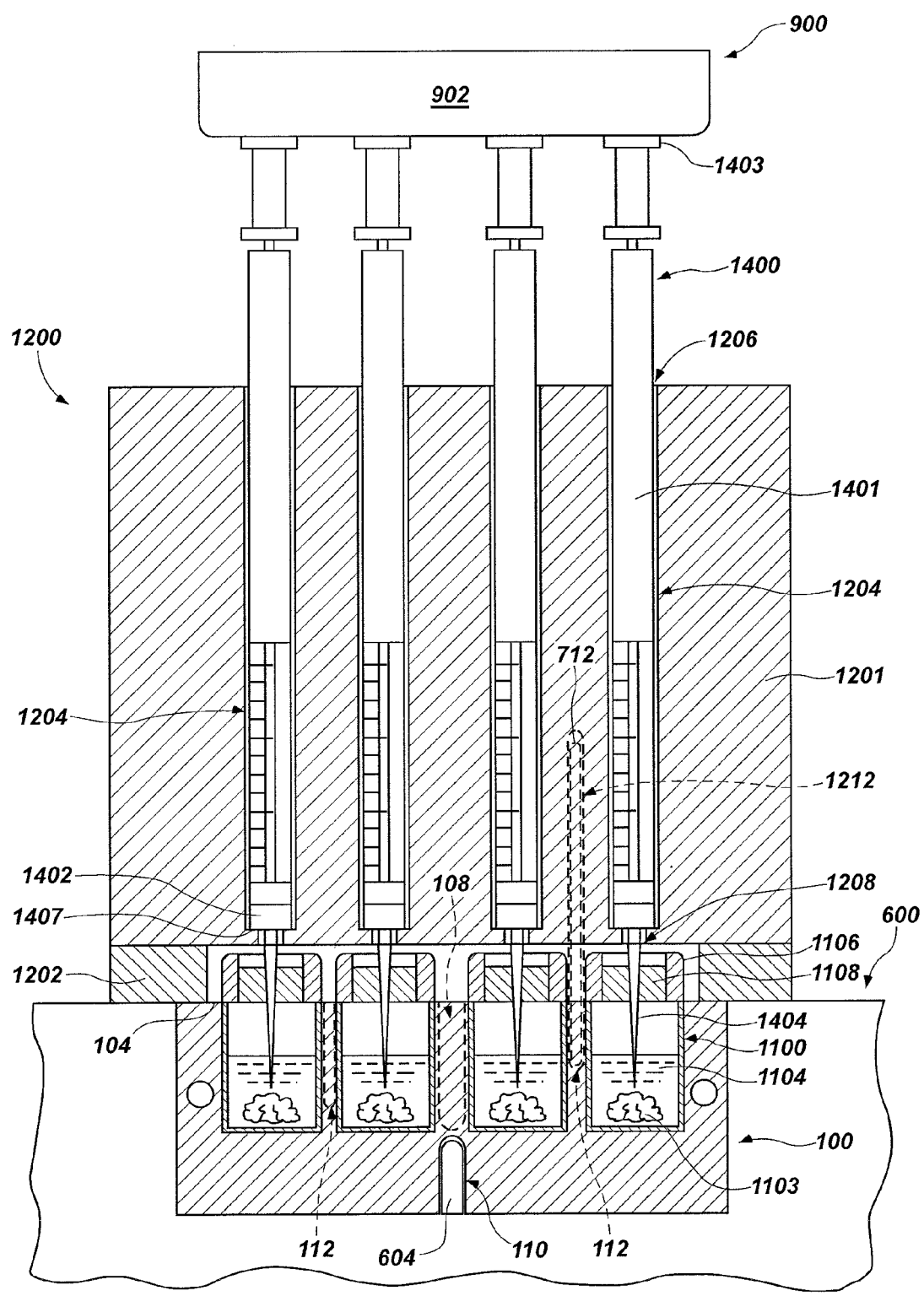

With continued reference to FIGS. 12 and 13 and with reference to FIG. 14, the supportive body 1201 may be substantially solid except for a number of conduits 1204 (FIG. 14) extending through a height of the supportive body 1201. Each of the conduits 1204 may extend between an upper opening 1206 and a lower opening 1208. A width of the upper opening 1206 may be greater than a width of the lower opening 1208. The width of the upper opening 1206 may be selected to receive therein a body 1401 of an injector (e.g., a syringe 1400), while the width of the lower opening 1208 may be selected to receive therein a needle 1404 extending from the injector (e.g., the syringe 1400).

The width of the conduit 1204 may transition, for example, step-wise from the width of the upper opening 1206 to the width of the lower opening 1208, such that a ledge 1407 surrounds the lower opening 1208. A lower end 1402 of the body 1401 of the injector (e.g., the syringe 1400) may rest against the ledge 1407 when the injector (e.g., the syringe 1400) is received within the conduit 1204, as illustrated in FIG. 14. The ledges 1407 of an arrangement of the conduits 1204 may be at equal heights, relative to the upper surface 104 of the conductive structure 100 when the injector support structure 1200 is positioned overhead.

The number and relative positioning of the conduits 1204 may correspond to the number and relative positioning of the wells 102 (FIG. 1) of the conductive structure 100. Thus, when the injector support structure 1200 is positioned over the conductive structure 100, the conduits 1204 and the reaction vessels 1100 or control vessels 1101 (FIG. 11) in the wells 102 align. In some embodiments, the supportive body 1201 of the injector support structure 1200 further defines therein an alignment opening 1212, as illustrated in FIGS. 13 and 14. The alignment opening 1212 may protrude upward, into the supportive body 1201 and be configured to receive therein an upper portion of the alignment member 712 extending from one of the openings 112 in the conductive structure 100. Therefore, to enable appropriate alignment of the conduits 1204 over the wells 102 (FIG. 1), the injector support structure 1200 may be positioned over the conductive structure 100 such that the alignment member 712 is received in the alignment opening 1212 of the supportive body 1201. In other embodiments, an alignment member (e.g., the alignment member 712) may be first received in the alignment opening 1212 of the supportive body 1201 and then received within the opening 112 of the conductive structure 100 when the injector support structure 1200 is positioned over the conductive structure 100. Thus, not only may the alignment member 712 enable securing of the lid 900 to the conductive structure 100 during heating, but the alignment member 712 may enable alignment of the injector support structure 1200 over the conductive structure 100 during enzyme addition.

As illustrated in FIG. 14, injectors (e.g., syringes 1400) may be positioned in the injector support structure 1200 such that the needles 1404 pass through the septa 1108 in the lids 1106 of the reaction vessels 1100 and down into the buffer fluid 1104 before at least one enzyme is simultaneously added to the reaction vessels 1100 via the injectors (e.g., syringes 1400) and into the buffer fluid 1104. Positioning the needles 1404 to a depth internal to the buffer fluid 1104 may inhibit the enzyme or enzymes from denaturing when passing through the narrow needles 1404.

In some embodiments, a flat surface that simultaneously contacts the tops of plungers 1403 of the injectors (e.g., the syringes 1400) may be used to simultaneously depress the plungers 1403 and expel the enzyme into the buffer fluid 1104. For example, an upper surface of the lid 900 may be used, as illustrated in FIG. 14. Thus, the enzyme or enzymes may be substantially simultaneously added to the reaction vessels 1100 to initiate the enzymatic reactions therein.

Because the injectors (e.g., the syringes 1400) may be pre-loaded into the conduits 1204 of the injector support structure 1200, because the injectors (e.g., the syringes 1400) may be positioned simultaneously as a group over the conductive structure 100, and because the injectors (e.g., the syringes 1400) may be simultaneously depressed to inject the contents thereof into the reaction vessels 1100, the addition of the enzyme or enzymes to the reaction vessels 1100 may be accomplished quickly. Thereafter, e.g., immediately thereafter, the injector support structure 1200 may be removed from over the conductive structure 100 and the lid 900 returned and secured to the conductive structure 100.

During the enzyme addition, heat may be continuously provided to the conductive structure 100 via the dry bath incubator 600. Therefore, the predetermined reaction temperature may be substantially maintained before, during, and after the enzyme addition. The temperature of the conductive structure 100 may be monitored, during the enzyme addition, via the thermocouple 604 in the thermocouple opening 110 of the conductive structure 100.

Because the enzyme or enzymes are added to the reaction vessels 1100 through the septa 1108 in the lids 1106, the closed volume of the reaction vessels 1100 remains sealed even during the enzyme addition. Thus, evaporation of reagents is prevented even during high-temperature processes.

Though FIG. 14 illustrates a row of four syringes 1400 received in a row of four conduits 1204 over four reaction vessels 1100, it is contemplated that even as few as one syringe 1400 may be utilized in the injector support structure 1200 over one reaction vessel 1100. Provided each syringe 1400 utilized in the injector support structure 1200 corresponds and aligns with one of the reaction vessels 1100 in the conductive structure 100, the number and relative positioning of the syringes 1400 may vary in different rows or columns of the injector support structure 1200 and/or in different runs using the injector support structure 1200.

More than one injector support structure 1200 may be simultaneously positioned and utilized in embodiments in which more than one conductive structure 100 is received in the dry bath incubator 600. Therefore, while FIG. 12, for example, illustrates one injector support structure 1200 over one of the two conductive structures 100 (FIG. 7) in the dry bath incubator 600, a second injector support structure 1200 may be positioned, simultaneously or sequentially, over the other of the conductive structures 100 (FIG. 7) and utilized sequentially or simultaneously. Alternatively, one injector support structure 1200 may be used to substantially simultaneously inject enzyme into reaction vessels 1100 of one of the conductive structures 100 (FIG. 7) and then repositioned over the other of the conductive structures 100 (FIG. 7) and used to substantially simultaneously inject enzyme into the reaction vessels 1100 of the other conductive structure 100 (FIG. 7). Because positioning the injector support structure 1200 over one conductive structure 100 may be quickly accomplished by sliding the alignment opening 1212 over the alignment member 712, the injector support structure 1200 can be quickly and easily positioned and repositioned, thus minimizing the time to add the enzyme and minimizing the time with the lid 900 (FIG. 14) off of the conductive structure 100.

After addition of the enzyme to the reaction vessels 1100, the lid 900 may be re-secured to the conductive structure 100, forming the conductive structure assembly 1000 (FIG. 10), which may then be agitated to encourage mixing of the substrate samples 1103 (FIG. 14) and the added enzyme. For example, the conductive structure assembly 1000 (FIG. 10) may be moved from the dry bath incubator 600 to an agitator (e.g., an orbital shaker, a reciprocal shaker) that may also be configured to provide heat during the agitation. In other embodiments, the dry bath incubator 600 and agitator may be integrated such that the conductive structure assembly 1000 may not need to be removed from a heating device (e.g., the dry bath incubator 600) to be agitated.

In some embodiments, the agitator may support the dry bath incubator 600 with the conductive structure assembly 1000 such that the conductive structure assembly 1000 may be agitated without removing the conductive structure assembly 1000 from the heating device (e.g., the dry bath incubator 600). Such agitator may be a movable surface (e.g., a shaker plate) supporting the dry bath incubator 600, a movable surface of the dry bath incubator 600 itself, or a container containing the dry bath incubator 600. The agitator may be configured to agitate the conductive structure assembly 1000 through a plane that is parallel to a length (e.g., a height) of the vessels (e.g., the reaction vessels 1100 and/or control vessels 1101) while the vessels are in the conductive structure assembly 1000 in the dry bath incubator 600. For example, the agitator may move the dry bath incubator 600 and the conductive structure assembly 1000 up and down, either vertically or along an orbit about a horizontal axis.

Alternatively, the system may be configured to rotate the dry bath incubator 600, the conductive structure assembly 1000, and, thus, the vessels (e.g., the reaction vessels 1100 and/or control vessels 1101) in the conductive structure assembly 1000 to align the length of the vessels along a substantially horizontal plane before horizontally agitating the conductive structure assembly 1000, either linearly or along an orbit about a vertical axis.

Figure 15:
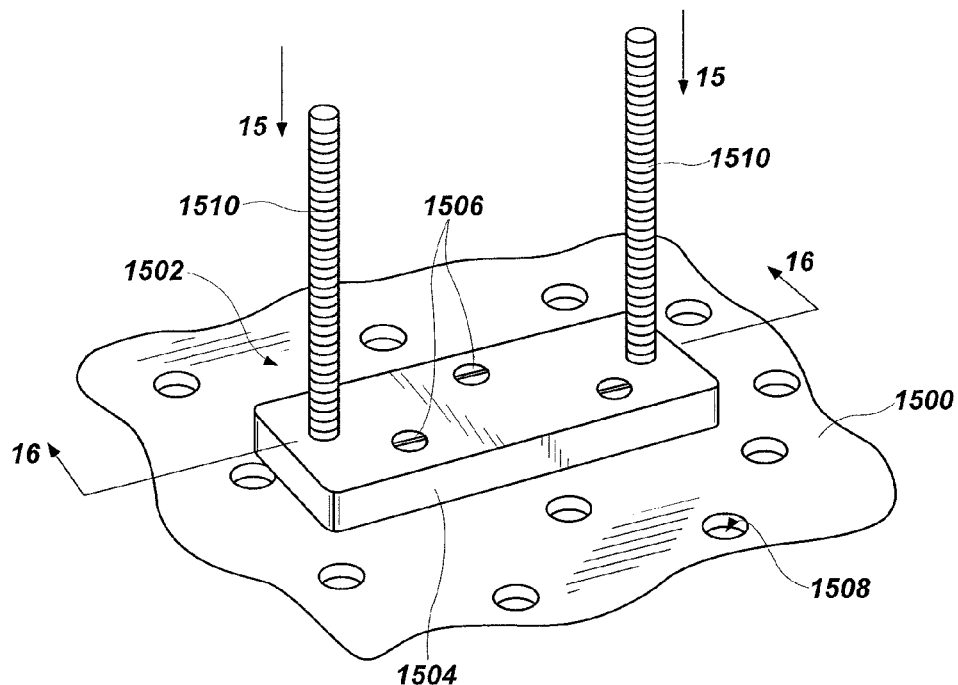

With reference to FIG. 15, in embodiments in which the agitator is separate from the dry bath incubator 600, the agitator may include a shaker plate 1500 to which the conductive structure 100 (FIG. 16) may be releaseably connected during agitation. In some embodiments, a support structure 1502 may be connected (e.g., releaseably connected) to the shaker plate 1500. The support structure 1502 may include a base plate 1504 mountable to the shaker plate 1500 via one or more fasteners 1506 extending through openings 1507 (FIG. 16) in the base plate 1504 and into openings 1508 in the shaker plate 1500. The fasteners 1506 may be configured as screws with threading corresponding to threads in the openings 1508. The shaker plate 1500 may be a component of a conventional and commercially available orbital shaker, such as a New Brunswick Scientific Model Innova 44R, and the openings 1507 in the base plate 1504 may be positioned to correspond to the openings 1508 in the shaker plate 1500 as acquired from its manufacturer. The fasteners 1506 utilized, however, may have a greater length, to accommodate a height of the base plate 1504, than those sold for use with the shaker plate 1500. The fasteners 1506 may be flush with a surface of the base plate 1504 when the base plate 1504 is secured to the shaker plate 1500, as illustrated in FIG. 15.

One or more engagement features 1510 may extend from the base plate 1504. The engagement features 1510 may be releaseably secured to the base plate 1504. For example, the engagement features 1510 may be threaded rods that may be screwed into threaded openings 1512 (FIG. 16) defined in the base plate 1504. In other embodiments, the engagement features 1510 may be permanently affixed to the base plate 1504.

Figure 16:
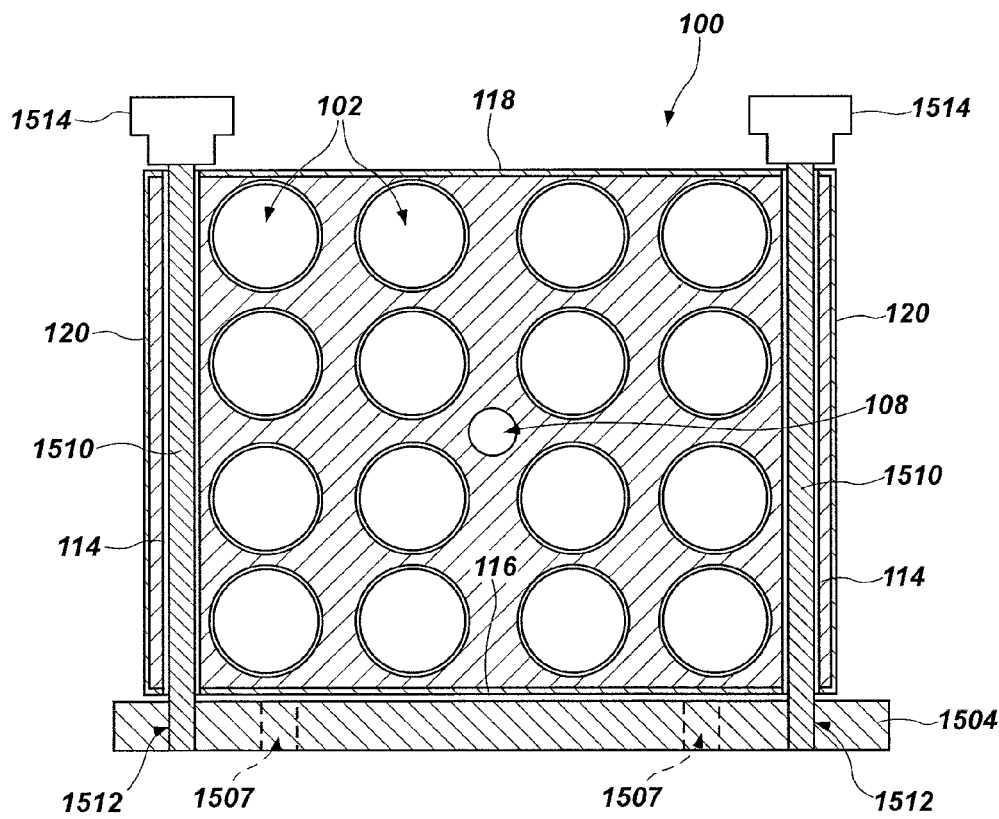

With reference to FIG. 16, the engagement features 1510 may be positioned to align with the openings 114 in the conductive structure 100. Thus, the engagement feature or features (e.g., the openings 114) of the conductive structure 100 may be selectively, slideably engaged (e.g., in the direction of arrows 15) with the counterpart engagement features (e.g., the engagement features 1510) on the support structure 1502 to mount the conductive structure 100 to the shaker plate 1500 during the agitation. In some embodiments, threaded caps 1514 may be attached and tightened over the ends of the engagement features 1510, which may protrude above the conductive structure 100, to further secure the conductive structure 100 in place.

Figure 17:
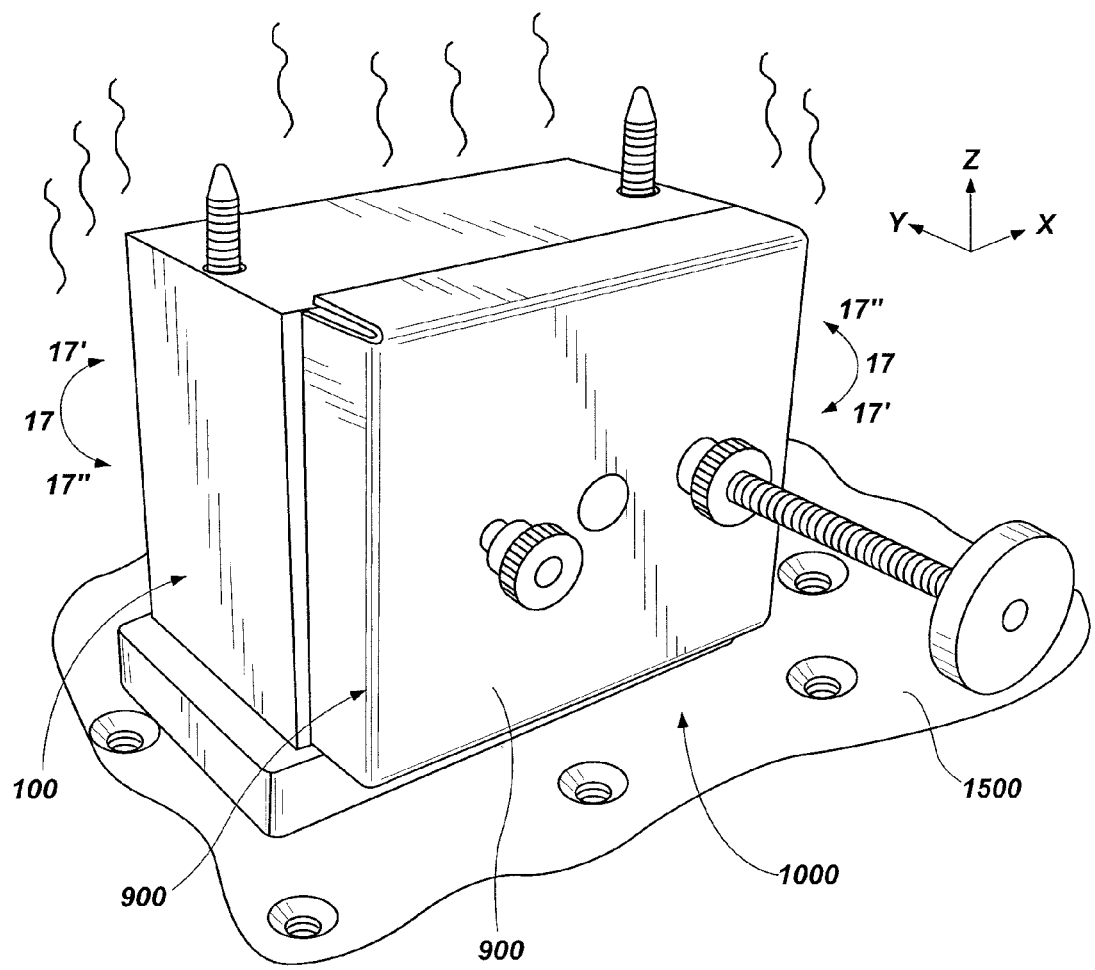

Because the engagement features (e.g., the openings 114) of the conductive structure 100 are defined in sidewalls (e.g., the front surface 116 and the back surface 118) of the conductive structure 100, when the conductive structure 100 is positioned on the engagement features 1510 of the support structure 1502, the upper surface 104 (FIG. 1) of the conductive structure 100 is essentially perpendicular to the shaker plate 1500 (FIG. 15). Thus, the reaction vessels 1100 (FIG. 11) and control vessels 1101 (FIG. 11) within the conductive structure 100 are positioned such that their length is parallel to the shaker plate 1500 (FIG. 15). With reference to FIG. 17, therefore, when the shaker plate 1500 orbits, e.g., in the direction of arrows 17 (e.g., in the direction of arrows 17', in the direction of arrows 17", or both alternatingly) in an x-y plane parallel to the surface of the shaker plate 1500, the conductive structure 100 and the reaction vessels 1100 (FIG. 11) and control vessels 1101 (FIG. 11) are agitated in a plane that is parallel to a length (e.g., a height) of each. Therefore, the substrate samples 1103 (FIG. 11) and the enzyme are mixed along one of the greatest available volume widths to promote better intermixing of the materials than may be achieved if the reaction vessels 1100 (FIG. 11) were agitated parallel to their width.

Heat may be provided while the conductive structure assembly 1000 is agitated so that the predetermined reaction temperature is maintained. The orbital shaker, in which the shaker plate 1500 is located, may be pre-heated to the predetermined reaction temperature before or while the conductive structure 100 is initially heated, the reaction vessels 1100 (FIG. 11) are heated, and the enzyme added. Therefore, as soon as the enzyme has been added to the conductive structure 100 and the lid 900 secured, the conductive structure assembly 1000 may be quickly moved to and positioned on the shaker plate 1500 without substantial heat loss during the transition. The orbital shaker may be closed around the conductive structure assembly 1000 during the agitation to retain the heat in the system.

Reaction time, following addition of the enzyme, may be monitored and samples taken from the reaction vessels 1100 (FIG. 11) and/or the control vessels 1101 (FIG. 11) at desired times to measure the enzymatic activity. For example, the reaction vessels 1100 (FIG. 11) may be transferred to ice or may be injected with a reaction-stopping agent to cease the enzymatic reaction at a desired time, and then contents of the reaction vessels 1100 (FIG. 11) may be analyzed. The stop time for one or more reaction vessels 1100 (FIG. 11) of the group of reaction vessels 1100 (FIG. 11) from the conductive structure assembly 1000 may be spaced from the stop time of others so as to analyze an enzymatic reaction at various times using one conductive structure 100 (FIG. 1). Therefore, the same process may be used and the agitation stage carried out for varying times to gather a range of enzyme reaction times.

The enzymatic reactions may be halted or substantially slowed, at the desired time, by removing the reaction vessels 1100 (FIG. 11) from the heated conductive structure 100 and moving them to ice, with the addition of reagents configured to halt the reaction, or both. Techniques for terminating enzymatic reactions are known in the art and so are not described in detail herein. The enzymatic activity may be determined according to techniques known in the art, which are also not described in detail herein. By way of non-limiting example, the enzymatic activity may be determined by a reducing sugar assay, high pressure liquid chromatography (HPLC), the Somogyi method, or the DNS method.

Because the methods and systems disclosed herein control the temperature of the system with closed volumes for the reaction vessels 1100 (FIG. 11), even during addition of the enzyme, high temperature reactions may be carried out without evaporation and, therefore, without skewed results. Moreover, because the methods and systems disclosed herein provide substantial intermixing of the substrate samples 1103 (FIG. 11) and the enzyme, insoluble substrates and substrates and enzymes that do not readily intermix may be analyzed without skewed results. Furthermore, because multiple small-volume samples may be simultaneously run in the conductive structure 100, even heterogeneous substrates and substrates or enzymes for which only small amounts are available may be analyzed for enzymatic activity.

EXAMPLE

Endo-1,4-β-XYLANASE M4 (hereinafter "Megazyme M4") is an enzyme commercially available from Megazyme International Ireland, Ltd., Wicklow, Ireland. The published specific activity for Megazyme M4, in association with a wheat arabinoxylan substrate, which is partially soluble, averages 79.3 U/mg Protein.

Figure 18:
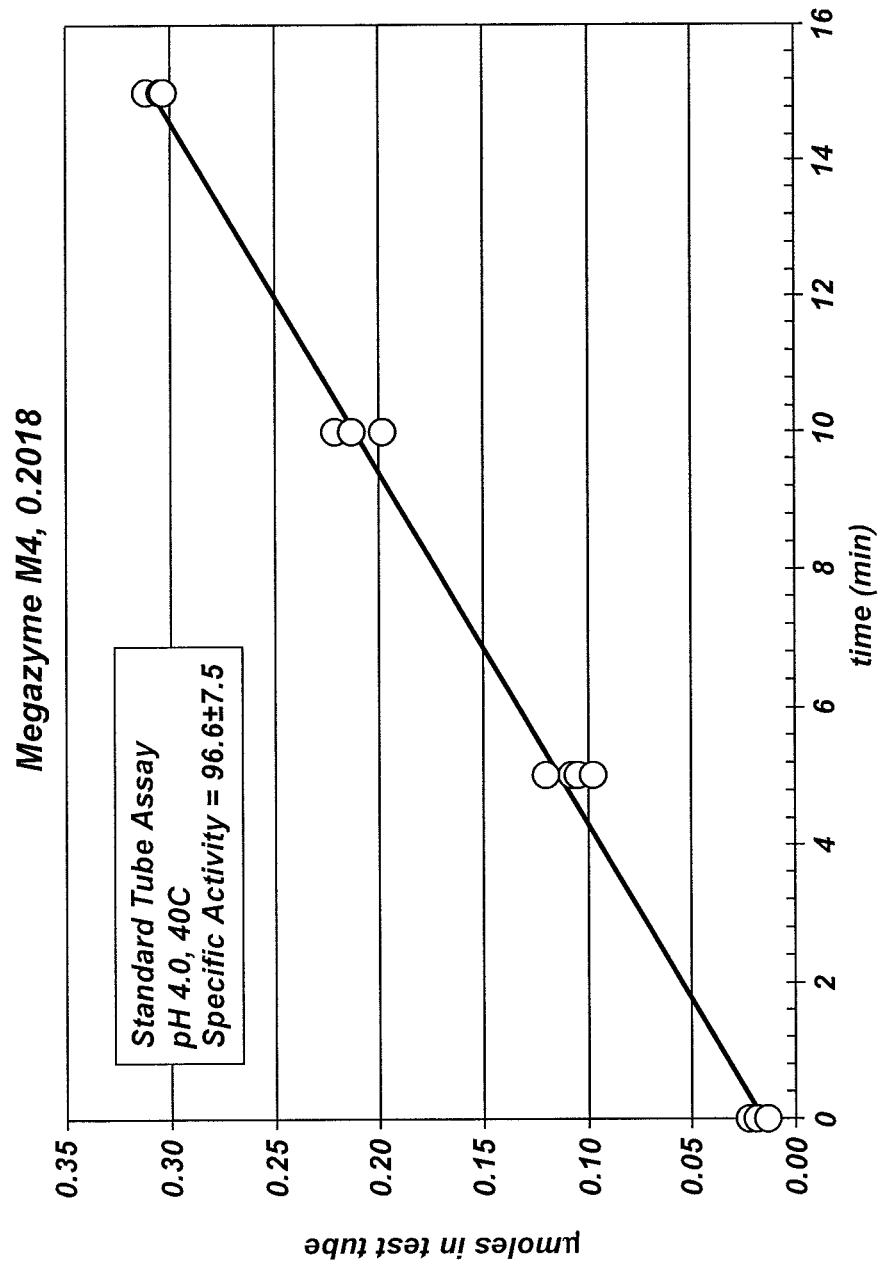
FIGS. 18 through 21 graph enzymatic activity results, for a commercially-available enzyme, determined using a conventional test tube assay that does not include agitation and sealed reaction vessels.
Figure 19:
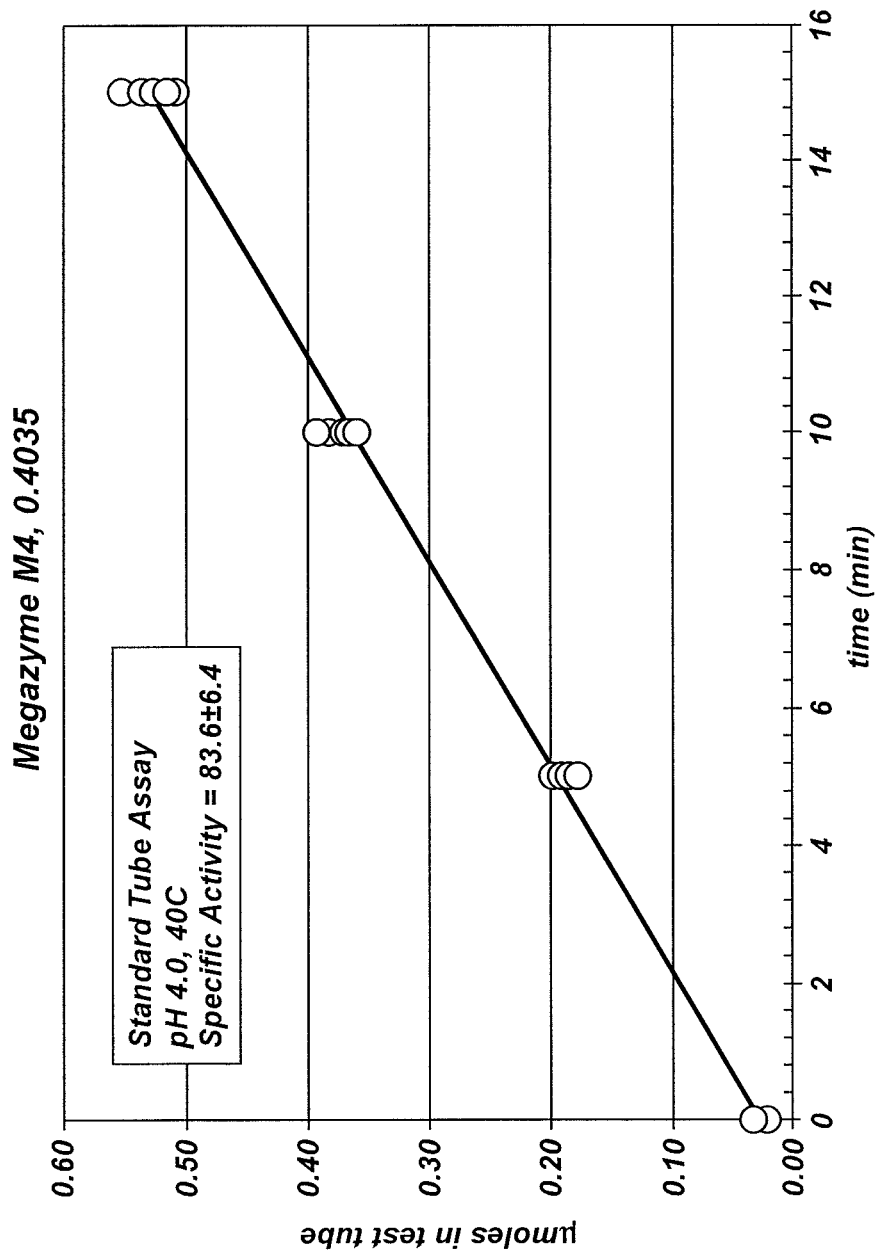
Figure 20:
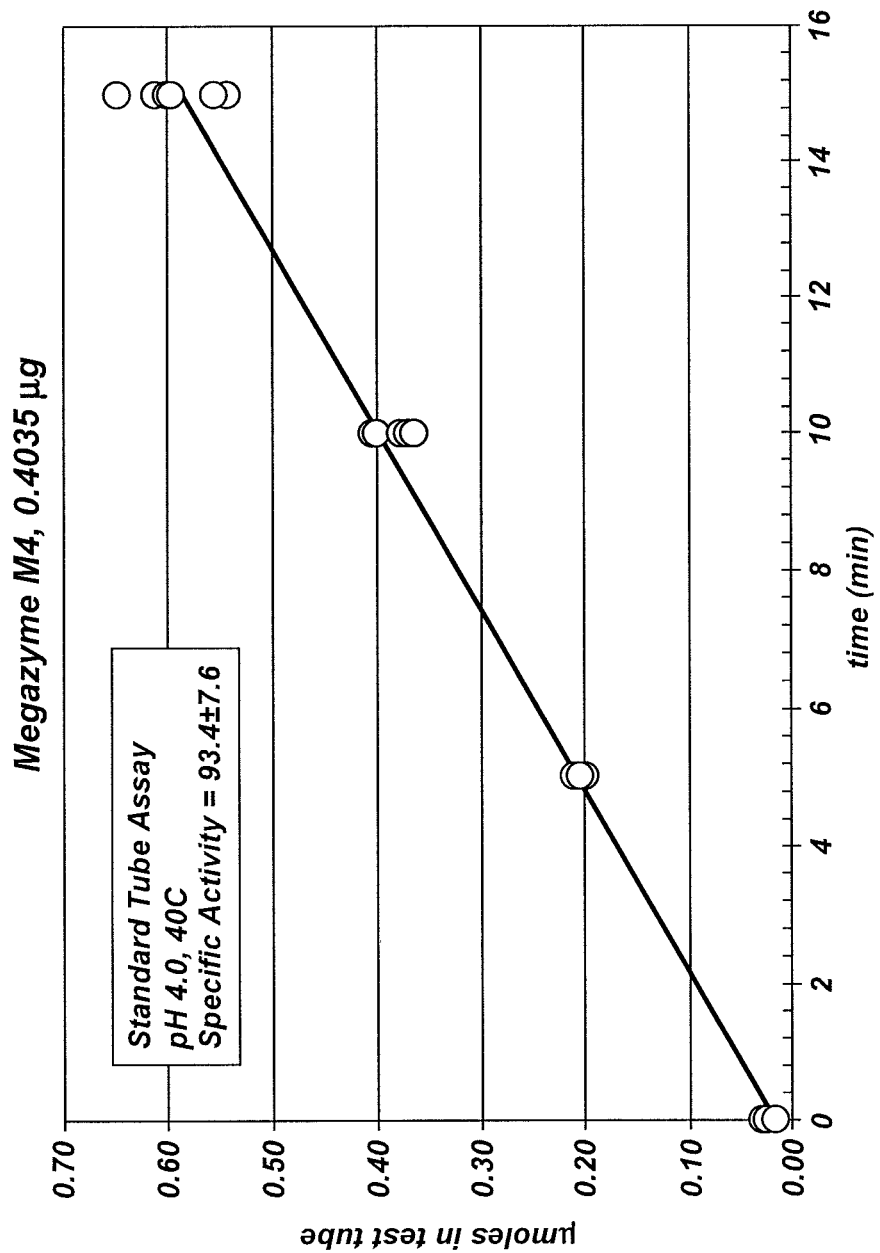
Figure 21:
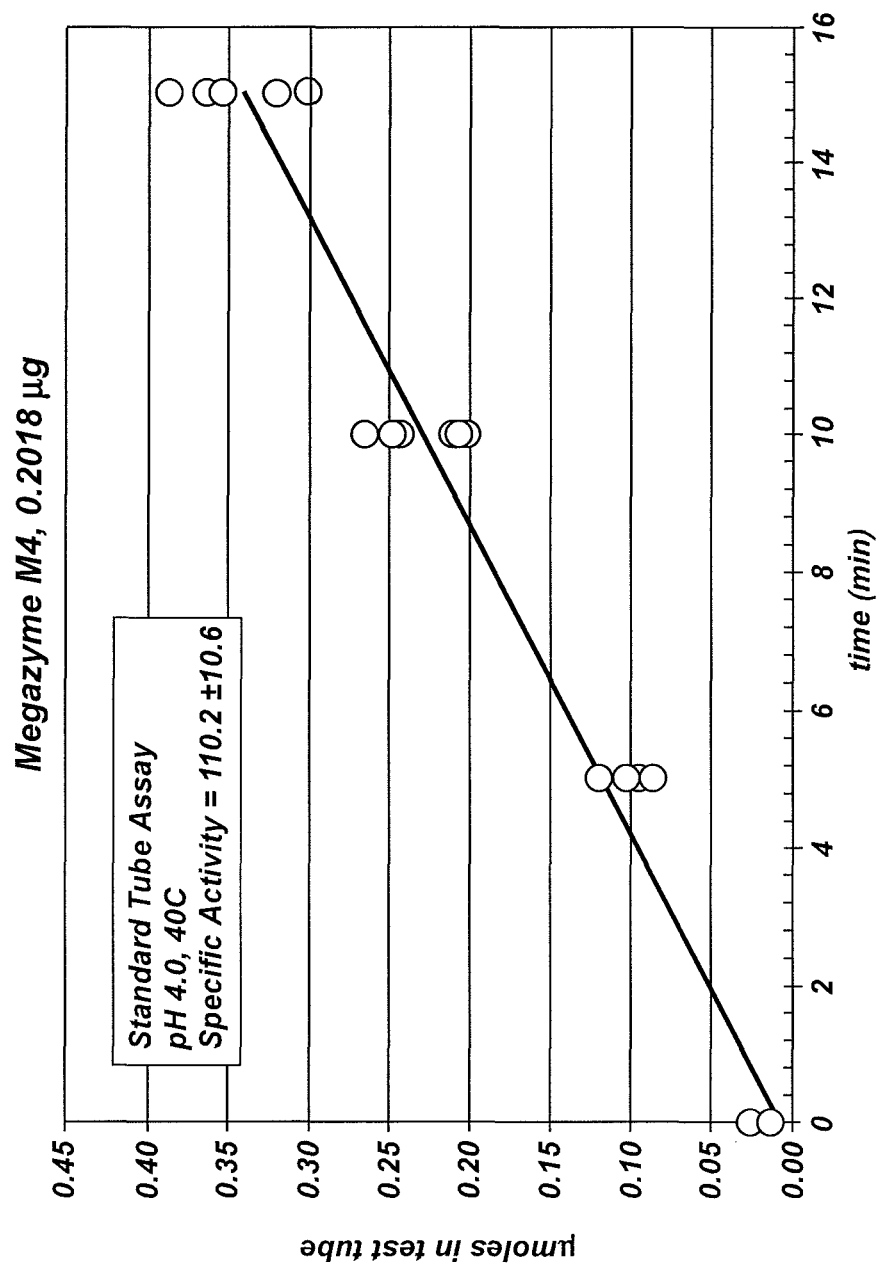

Enzymatic reactions with various volumes of Megazyme M4 and various amounts of wheat arabinoxylan were carried out, according to a conventional test tube assay that does not include agitation or sealed reaction vessels, and then activity determined at various reaction times according to a standard Somogyi characterization method. All reactions used a substrate solution at a pH of 4.0 and a reaction temperature of 40° C. Results are shown in FIGS. 18 through 21, which plot amount of reaction product (in μmoles) against reaction stop time (in minutes). With reference to FIG. 18, using 0.2018 μg of the enzyme, the specific activity was measured at 96.6±7.5 U/mg. With reference to FIG. 19, using 0.4035 μg of the enzyme, the specific activity was measured at 83.6±6.4 U/mg. With reference to FIG. 20, also using 0.4035 μg of the enzyme, the specific activity was measured at 93.4±7.6 U/mg. With reference to FIG. 21, again using 0.2018 μg of the enzyme, the specific activity was measured at 110.2±10.6 U/mg. As summarized in Table I below, the conventional standard tube assay yielded enzymatic activities that were, on average, about 16.6 U/mg higher (plus or minus between 6.4 U/mg and 10.6 U/mg) than the enzymatic activity reported by the commercial supplier (79.3 U/mg).

TABLE I (Standard Tube Assay)

| Amount of Enzyme (μg) | Determined Activity (U/mg) | Difference from Published Activity of 79.3 U/mg |
|---|---|---|
| 0.2018 | 96.6 ± 7.5 (FIG. 18) | 17.3 ± 7.5 |
| 0.2018 | 110.2 ± 10.6 (FIG. 21) | 30.9 ± 10.6 |
| 0.4035 | 83.6 ± 6.4 (FIG. 19) | 4.3 ± 6.4 |
| 0.4035 | 93.4 ± 7.6 (FIG. 20) | 14.1 ± 7.6 |
| Average | 96.0 | 16.6 |

Figure 22:
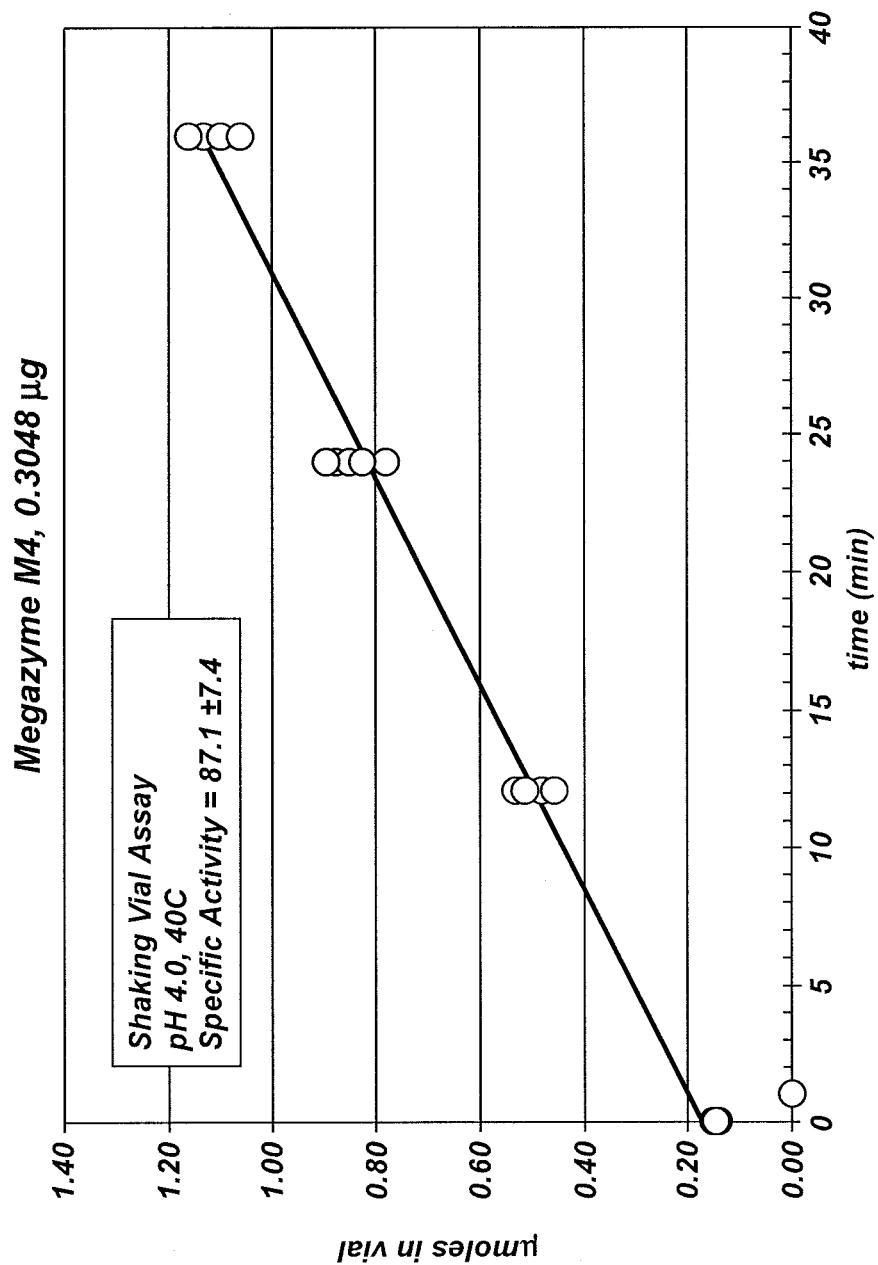
FIGS. 22 through 25 graph enzymatic activity results, for the commercially-available enzyme, determined using a method according to the present disclosure that includes agitation and sealed reaction vessels.
Figure 23:
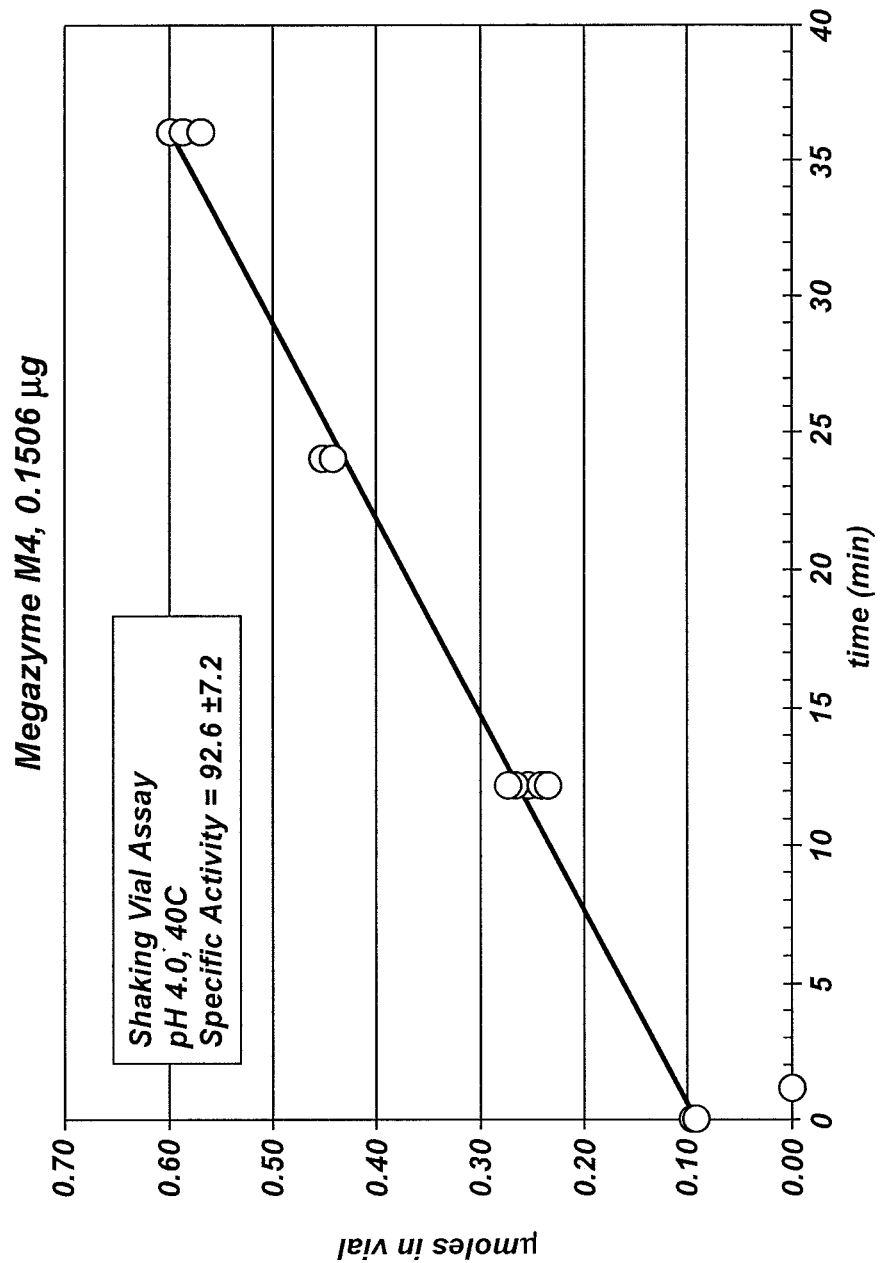
Figure 24:
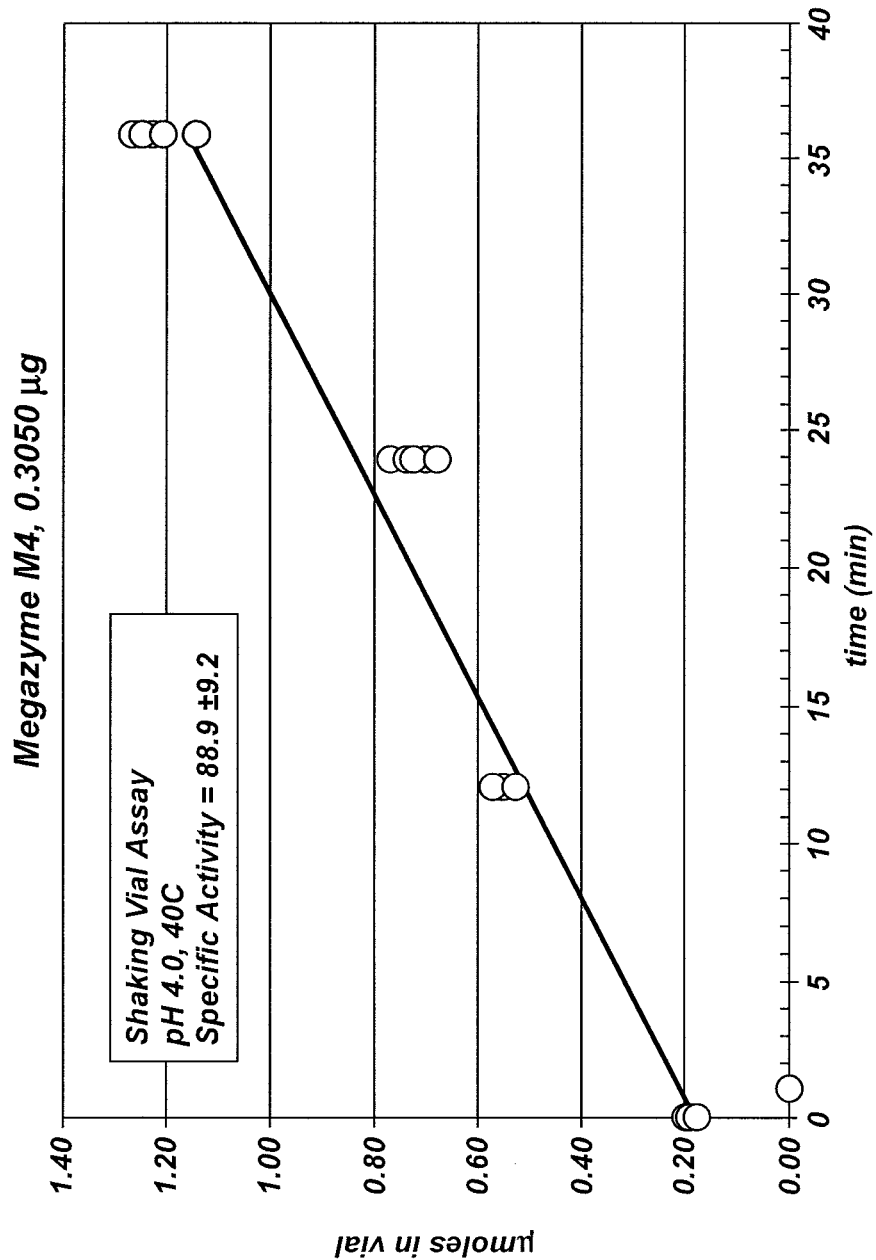
Figure 25:
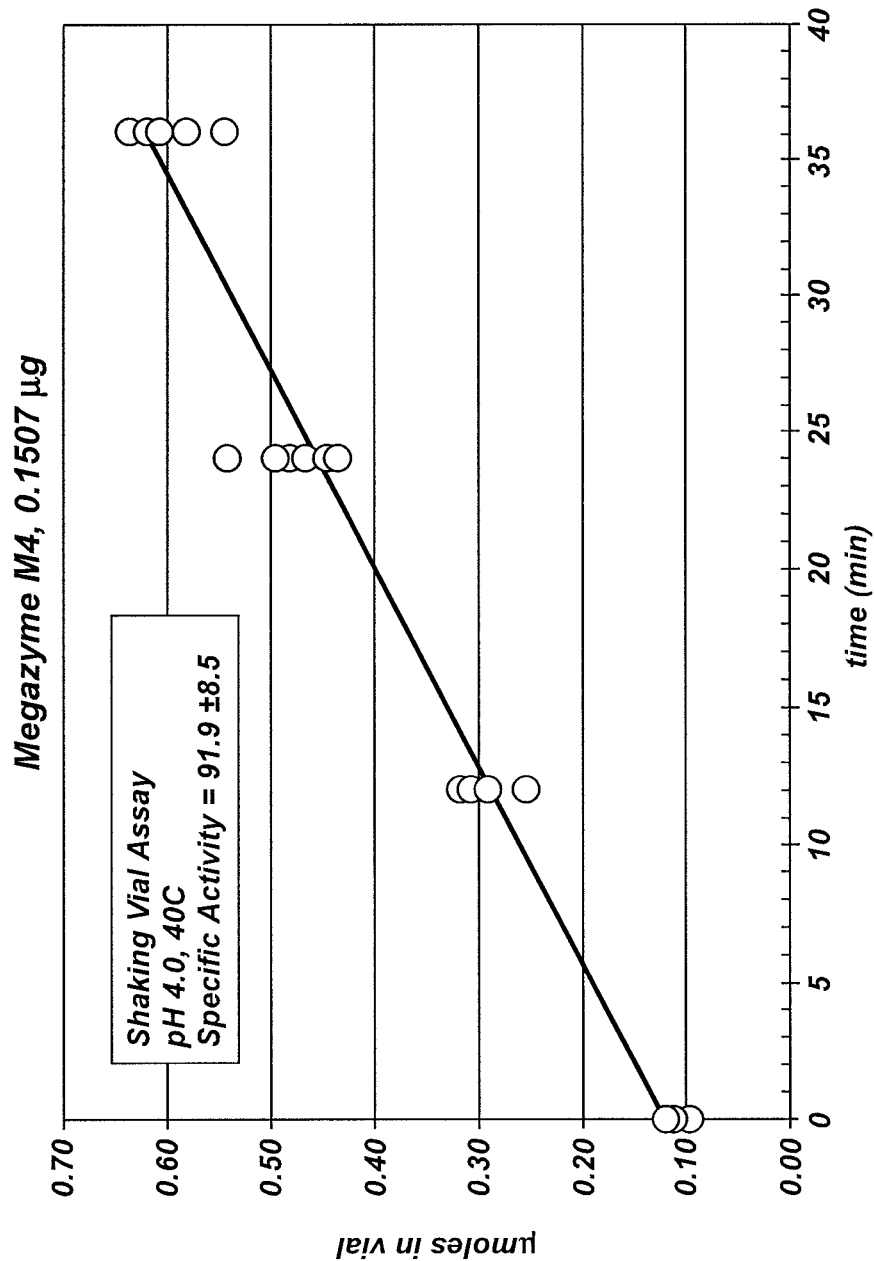

Enzymatic reactions with various volumes of Megazyme M4 and various amounts of wheat arabinoxylan were then carried out according to the sealed vessel with agitation method according to embodiments of the present disclosure, and then activity was determined at various times according to the standard Somogyi characterization methods. All reactions used a substrate solution at a pH of 4.0 and a reaction temperature of 40° C. Results are shown in FIGS. 22 through 25, which plot amount of reaction product (in μmoles) against reaction stop time (in minutes). With reference to FIG. 22, using 0.3048 μg of the enzyme, the specific activity was measured at 87.1±7.4 U/mg. With reference to FIG. 23, using 0.1506 μg of the enzyme, the specific activity was measured at 92.6±7.2 U/mg. With reference to FIG. 24, using 0.3050 μg of the enzyme, the specific activity was measured at 88.9±9.2 U/mg. With reference to FIG. 25, using 0.1507 μg of the enzyme, the specific activity was measured at 91.9±8.5 U/mg. As summarized in Table II below, the method according to the present disclosure yielded enzymatic activities that were, on average, only about 10.8 U/mg higher (plus or minus between 7.2 U/mg and 9.2 U/mg) than the enzymatic activity reported by the commercial supplier (79.3 U/mg), even at lower enzyme amounts than used with the standard tube assay.

TABLE II (Sealed Vial with Agitation Assay)

| Amount of Enzyme (μg) | Determined Activity (U/mg) | Difference from Published Activity of 79.3 U/mg |
|---|---|---|
| 0.1506 | 92.6 ± 7.2 (FIG. 23) | 13.3 ± 7.2 |
| 0.1507 | 91.9 ± 8.5 (FIG. 25) | 12.6 ± 8.5 |
| 0.3048 | 87.1 ± 7.4 (FIG. 22) | 7.8 ± 7.4 |
| 0.3050 | 88.9 ± 9.2 (FIG. 24) | 9.6 ± 9.2 |
| Average | 90.1 | 10.8 |

Thus, the methods of the present disclosure yielded enzymatic activities that were, on average, closer to the specific activity of the enzyme reported by the commercial supplier than the enzymatic activities determined using a conventional tube assay. Accordingly, the methods of the present disclosure may yield more accurate results, for a partially-soluble substrate in very small amounts, than methods that do not use agitation.

Notably, the demonstrated improvement may be achieved with even moderate-temperature enzymatic reactions such as the 40° C. reactions of the examples of FIGS. 22 through 25. Therefore, though the methods of the present disclosure may be well suited for high-temperature enzymatic reactions, because the methods may avoid skewing due to evaporation, the example discussed here demonstrates that the methods are also effective for moderate-temperature enzymatic reactions.

While the disclosed methods and systems are susceptible to various modifications and alternative forms in implementation thereof, specific embodiments have been shown by way of example in the drawings and have been described in detail herein. However, it should be understood that the present disclosure is not intended to be limited to the particular forms disclosed. Rather, the disclosed methods and systems encompass all modifications, combinations, equivalents, variations, and alternatives falling within the scope of the present disclosure as defined by the following appended claims and their legal equivalents.

What is claimed is:

1. A method for determining enzymatic activity, the method comprising:
   heating a substrate solution in a plurality of closed volumes to at least a predetermined reaction temperature;
   without opening the closed volumes of the plurality, substantially simultaneously adding at least one enzyme to the closed volumes of the plurality;
   while heating the closed volumes of the plurality to maintain at least the predetermined reaction temperature, agitating the plurality of closed volumes after adding the at least one enzyme; and
   after agitating, determining activity of the at least one enzyme.

2. The method of claim 1, wherein heating a substrate solution in a plurality of closed volumes to at least a predetermined reaction temperature comprises:
   adding substrate samples to the plurality of closed volumes;
   inserting the plurality of closed volumes in a plurality of wells defined in a conductive structure; and
   heating the conductive structure to at least the predetermined reaction temperature.

3. The method of claim 1, wherein heating a substrate solution in a plurality of closed volumes to at least a predetermined reaction temperature comprises:
   heating a conductive structure to at least the predetermined reaction temperature, the conductive structure supporting a plurality of vessels each containing a volume of heat transfer fluid;
   replacing at least some of the plurality of vessels with the plurality of closed volumes containing the substrate solution; and
   continuing heating of the conductive structure with the plurality of closed volumes until at least the predetermined reaction temperature is reached.

4. The method of claim 1, wherein substantially simultaneously adding at least one enzyme to the closed volumes of the plurality comprises:
   positioning injectors, containing the at least one enzyme, over the closed volumes of the plurality; and
   substantially simultaneously injecting the at least one enzyme from the injectors into a buffer fluid in the closed volumes of the plurality.

5. The method of claim 4, wherein positioning injectors, containing the at least one enzyme, over the closed volumes of the plurality comprises inserting the injectors into conduits defined in an injector support structure to rest a body of each of the injectors against a ledge defined within the conduits.

6. The method of claim 1, wherein substantially simultaneously adding at least one enzyme to the closed volumes of the plurality comprises substantially simultaneously adding the at least one enzyme to the closed volumes of the plurality while the closed volumes are maintained at at least the predetermined reaction temperature.

7. The method of claim 1, wherein agitating the plurality of closed volumes after adding the at least one enzyme comprises orbitally shaking or reciprocally shaking the plurality of closed volumes along a plane parallel to a length of the plurality of closed volumes.

8. A method for determining enzymatic activity, the method comprising:
heating to at least a predetermined reaction temperature a conductive structure supporting sealed reaction vessels containing substrate;
substantially simultaneously injecting at least one enzyme into the sealed reaction vessels;
while heating the conductive structure, agitating the conductive structure supporting the sealed reaction vessels with the substrate and the at least one enzyme in a plane of motion parallel to a length of the sealed reaction vessels; and
determining activity of the at least one enzyme.

9. The method of claim 8, wherein heating to at least a predetermined reaction temperature a conductive structure comprises inserting the conductive structure into a cavity of a dry bath incubator.

10. The method of claim 9, wherein substantially simultaneously injecting at least one enzyme into the sealed reaction vessels comprises substantially simultaneously injecting the at least one enzyme into the sealed reaction vessels through septa while the conductive structure remains in the cavity of the dry bath incubator.

11. The method of claim 9, wherein agitating the conductive structure supporting the sealed reaction vessels with the substrate and the at least one enzyme in a plane of motion parallel to a length of the scaled reaction vessels comprises moving the conductive structure from the dry bath incubator to a heated orbital shaker.

12. The method of claim 8, wherein heating to at least a predetermined reaction temperature a conductive structure supporting sealed reaction vessels containing substrate comprises heating to at least the predetermined reaction temperature a conductive structure defined by an essentially-solid block of conductive material defining wells supporting the sealed reaction vessels.

13. A method for determining enzymatic activity, the method comprising:
heating a structure comprising vessels to at least a predetermined reaction temperature;
replacing the vessels with other vessels, at least some vessels of the other vessels comprising a substrate sample in a fluid and sealed with a penetrable lid;
at at least the predetermined reaction temperature and without opening the other vessels, injecting, through the penetrable lid and into the fluid, at least one enzyme;
while heating the structure comprising the other vessels, moving the other vessels through a horizontal plane to intermix the substrate sample and the at least one enzyme; and
determining activity of the at least one enzyme.

14. The method of claim 13, wherein heating a structure comprising vessels to at least a predetermined reaction temperature comprises heating the structure comprising the vessels to a temperature above about 50° C.

15. The method of claim 13, further comprising, prior to heating the structure, adding to the vessels water or oil of a volume about equal to a volume of the fluid in the at least some vessels of the other vessels.

16. The method of claim 13, further comprising, before the injecting, inserting injectors in an injector support structure, the injectors comprising the at least one enzyme to be injected into the fluid.

17. The method of claim 16, wherein injecting, through the penetrable lid and into the fluid, at least one enzyme comprises passing a needle of each of the injectors through the penetrable lid and into the fluid.

18. The method of claim 17, wherein injecting, through the penetrable lid and into the fluid, at least one enzyme further comprises, after passing the needle, substantially simultaneously depressing plungers of the injectors to dispense the at least one enzyme into the fluid.

19. The method of claim 13, further comprising, before moving the other vessels through a horizontal plane, rotating the other vessels, while supported by the structure, about ninety degrees to align a height of the other vessels parallel to the horizontal plane.

20. The method of claim 13, wherein injecting, through the penetrable lid and into the fluid, at least one enzyme comprises injecting about 0.15 micrograms to about 0.30 micrograms of the at least one enzyme into the fluid.

\* \* \* \* \*